US009078335B2

(12) United States Patent
Sugahara et al.

(10) Patent No.: US 9,078,335 B2
(45) Date of Patent: Jul. 7, 2015

(54) CHARGED PARTICLE BEAM TRANSPORT SYSTEM AND PARTICLE BEAM THERAPY SYSTEM

(75) Inventors: Kengo Sugahara, Chiyoda-ku (JP); Shuhei Odawara, Chiyoda-ku (JP); Katsuhisa Yoshida, Chiyoda-ku (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/382,637

(22) PCT Filed: May 24, 2012

(86) PCT No.: PCT/JP2012/063268
§ 371 (c)(1),
(2), (4) Date: Sep. 3, 2014

(87) PCT Pub. No.: WO2013/175600
PCT Pub. Date: Nov. 28, 2013

(65) Prior Publication Data
US 2015/0038764 A1 Feb. 5, 2015

(51) Int. Cl.
*A61N 5/10* (2006.01)
*H05H 7/04* (2006.01)
*H05H 11/00* (2006.01)
*H05H 13/04* (2006.01)
*H05H 7/00* (2006.01)

(52) U.S. Cl.
CPC ........... *H05H 7/04* (2013.01); *H05H 2007/048* (2013.01); *H05H 2277/11* (2013.01); *A61N 5/1079* (2013.01); *A61N 5/1081* (2013.01); *A61N 2005/1087* (2013.01); *A61N 5/1042* (2013.01); *H05H 11/00* (2013.01);

(Continued)

(58) Field of Classification Search
USPC ....................................................... 250/492.3
See application file for complete search history.

(56) References Cited

U.S. PATENT DOCUMENTS 6,476,403 B1  11/2002  Dolinskii et al.
2003/0183779 A1  10/2003  Norimine et al.

(Continued)

FOREIGN PATENT DOCUMENTS

JP  9-265000 A  10/1997
JP  11-174198 A  7/1999

(Continued)

OTHER PUBLICATIONS

International Search Report (PCT/ISA/210) mailed on Aug. 28, 2012, by the Japanese Patent Office as the International Searching Authority for International Application No. PCT/JP2012/063268.

*Primary Examiner* — Kiet T Nguyen
(74) *Attorney, Agent, or Firm* — Buchanan Ingersoll & Rooney PC

(57) ABSTRACT

A charged particle beam transport system is characterized in that in a fixed transport unit, a phase of a phase space distribution of a charged particle beam at an inlet of a rotating deflection unit that rotates around an gantry rotation axle of a rotating gantry coincides with a phase determined by a calculation based on an average value of a first phase advance and a second phase advance. The first phase advance is defined as a change in a phase, of the phase space distribution, that changes when the charged particle beam travels from the inlet of the rotating deflection unit to an isocenter in the case where a gantry angle is a gantry reference angle; the second phase advance is defined as a change in a phase at a time when the gantry angle is pivoted by 90° from the gantry reference angle.

18 Claims, 21 Drawing Sheets

(52) U.S. Cl.
CPC ........ *H05H 13/04* (2013.01); *H05H 2007/046* (2013.01); *H05H 7/001* (2013.01); *H05H 2007/002* (2013.01)

(56) References Cited

U.S. PATENT DOCUMENTS

2004/0232356 A1 11/2004 Norimine et al.
2005/0247890 A1 11/2005 Norimine et al.
2009/0283702 A1* 11/2009 Umezawa et al. ......... 250/492.3

FOREIGN PATENT DOCUMENTS

| | | |
|---|---|---|
| JP | 2002-541464 A | 12/2002 |
| JP | 2003-282300 A | 10/2003 |
| JP | 2005-329252 A | 12/2005 |
| JP | 2006-351339 A | 12/2006 |

* cited by examiner

FIG. 4
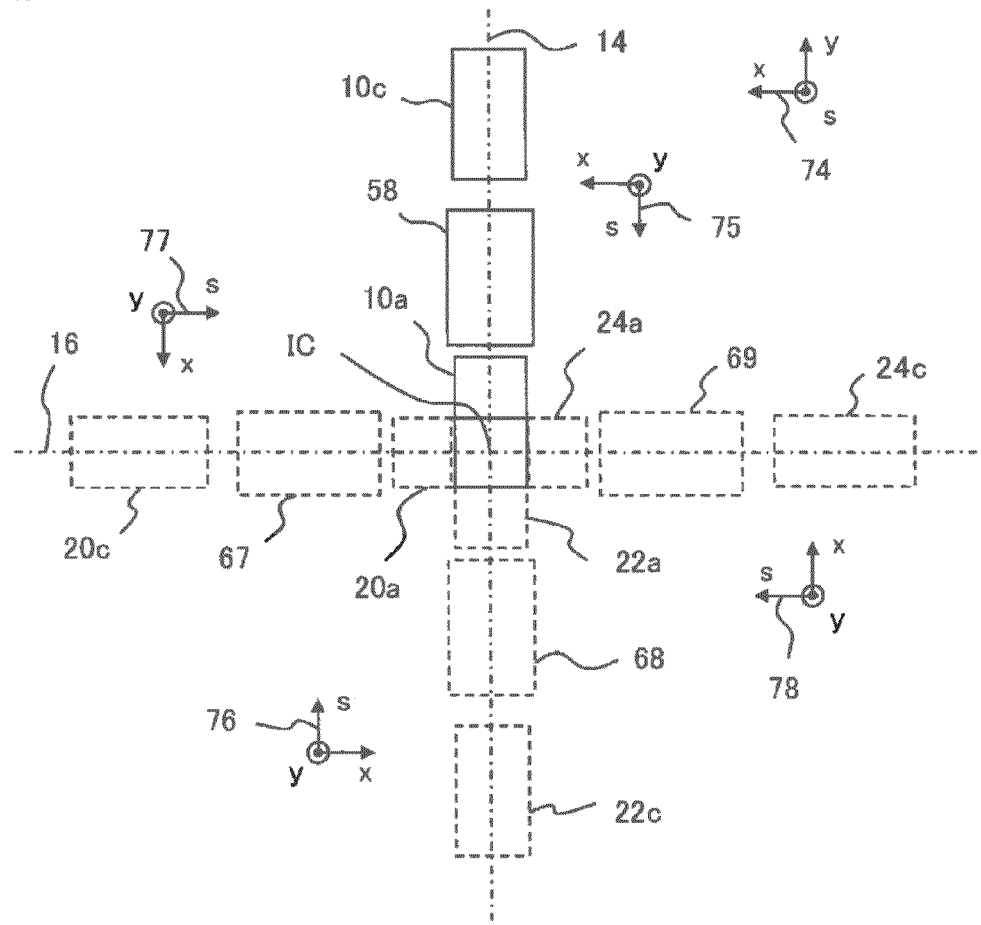
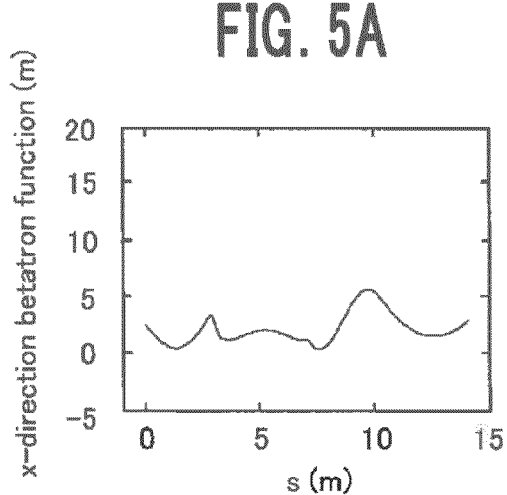
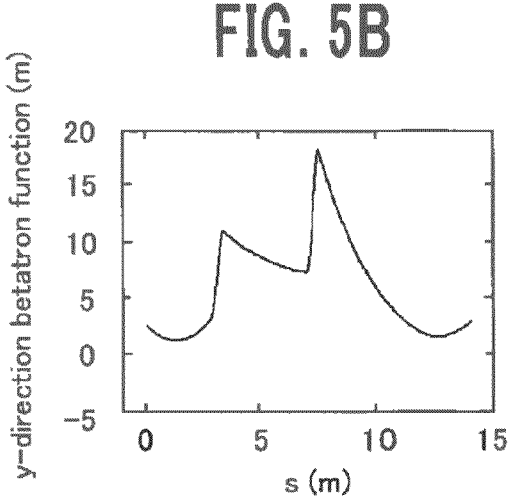
FIG. 5A
FIG. 5B

CHARGED PARTICLE BEAM TRANSPORT SYSTEM AND PARTICLE BEAM THERAPY SYSTEM

TECHNICAL FIELD

The present invention relates to a charged particle beam transport system that transports a charged particle beam formed of a charged particle such as a proton or a heavy particle and to a particle beam therapy system that irradiates a transported charged particle beam onto a to-be-irradiated object such as an object or a human body.

BACKGROUND ART

In general, a particle beam therapy system is provided with a beam generation apparatus that generates a charged particle beam, an accelerator that is connected with the beam generation apparatus and accelerates a generated charged particle beam, a charged particle beam transport system that transports a charged particle beam that is accelerated by the accelerator so as to gain predetermined energy and then is emitted, and a particle beam irradiation apparatus, disposed at the downstream side of the beam transport system, for irradiating a charged particle beam onto an irradiation subject.

In general, the motion of a charged particle in a charged particle beam in a charged particle beam transport system is described based on a coordinate system in which s direction is the traveling direction of a beam, x direction is a direction that is perpendicular to s direction and is the deflection direction of an accelerator, and y direction is a direction perpendicular to both direction and x direction. In this situation, the distribution of a charged particle in a beam in the charged particle beam transport system is not uniform. In general, in the case of a slow-extraction method in which a beam is slowly extracted from the synchrotron, which is an accelerator, the y-direction distribution of a charged particle is a Gaussian distribution, and the x-direction distribution thereof is a non-Gaussian distribution; thus, the respective emittances corresponding to the x-direction and y-direction areas in the phase space of the beam are asymmetric with each other. The slow-extraction method denotes a method in which charged particle beams are extracted little by little from a synchrotron over a long period.

When attention is focused on the motions of charged particle, the respective traveling directions thereof are different from each other and change with time; the beams, as a whole, perform a constant-period oscillation that is called a betatron oscillation. The angle and the width of the beam ellipse of a charged particle beam in a phase space can be changed by a quadrupole electromagnet or the like; however, even in this case, the emittance (the area of the ellipse) is kept constant. In general, in a charged particle beam transport system, the x-direction and y-direction emittances are asymmetric with each other, and this difference cannot be cancelled even by the quadrupole electromagnet or the like.

As described above, the emittances are asymmetric with each other; therefore, when the treatment plan for a particle beam therapy is made, it is difficult to secure the uniformity of a dose irradiated onto a diseased site. That is to say, the fact that the distribution of x-direction charged particles on a diseased site is a non-Gaussian distribution makes treatment planning complicated and makes an actually irradiated dose non-uniform, although the non-uniformity is within a tolerance range. When it is required to reduce the exposure amount of normal tissues as much as possible while a particle beam is intensively irradiated onto a diseased site, it is preferable to utilize a rotating gantry for rotating a particle beam irradiation apparatus around the patient. However, when there exists the non-uniformity of emittance, the spot shape of a beam on the diseased site changes depending on the rotation angle of the rotating gantry, thereby making treatment planning difficult.

Patent Document 1 discloses a charged particle beam transport system that is provided with an emittance adjustment means such as a skew quadrupole electromagnet or a solenoid electromagnet, for the purpose of symmetrizing the emittances. Patent Document 2 discloses a charged particle beam irradiation apparatus that is provided with a scatterer and a downstream electromagnet formed of a plurality of quadrupole electromagnets provided at the downstream side of the scatterer in a charged particle beam transport system. The scatterer and the downstream electromagnet symmetrize the emittances and make each of the x-direction and y-direction distributions of charged particles become a Gaussian distribution.

PRIOR ART REFERENCE

Patent Document

[Patent Document 1] Japanese Patent Application Laid-Open No. H9-265000 (paragraphs [0005] through [0009], FIG. 1)
[Patent Document 2] Japanese Patent Application Laid-Open No. 2006-351339 (paragraphs [0011] through [0013], FIG. 3)

DISCLOSURE OF THE INVENTION

Problems to be Solved by the Invention

To date, in order to prevent the spot shape of a beam on the diseased site of a patient from changing depending on the rotation angle of the rotating gantry, an emittance adjustment means for symmetrizing the emittances, a scatterer, and a downstream electromagnet have been provided, before the deflection electromagnet, in the charged particle beam transport system. Because an emittance adjustment means, a scatterer, and a downstream electromagnet have been added to a conventional charged particle beam transport system, there has been a problem that the charged particle beam transport system is upsized.

The present invention has been implemented in order to solve the foregoing problem; the objective thereof is to make a charged particle beam transport system absorb the difference in emittances, caused when a beam is launched from an accelerator in a slow-extraction manner, and to realize a beam size having a small rotation dependency at an isocenter.

Means for Solving the Problems

A charged particle beam transport system according to the present invention transports a charged particle beam to a particle beam irradiation apparatus mounted in a rotating gantry capable of rotating around an isocenter; letting an x direction denote a direction on a circular orbit plane of an accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam launched from the accelerator is a charged particle beam whose x-direction and y-direction emittances are different from each other; the charged particle beam transport system includes a rotating deflection unit that is mounted in the rotating gantry and rotates around a gantry rotation axle of the rotating gantry and a fixed transport unit ranging from the accelerator to the rotating deflection unit; the rotating deflection unit includes two or more deflection electromagnets, fixed transport unit includes two or more quadrupole electromagnets. The charged particle beam transport system according to the present invention is characterized in that when viewed from the gantry rotation axle, a gantry angle is defined as an angle between a beam center line of the particle beam irradiation apparatus and y-direction axis of the charged particle beam at an inlet of the rotating deflection unit, in that a gantry reference angle is defined as an angle of the rotating gantry at which the charged particle beam is transported in such a way that x-direction and y-direction emittances at the launching position of the accelerator are separated and the respective emittances are maintained, in that a first phase advance is defined as a change in a phase, of a phase space distribution of the charged particle beam, that changes when the charged particle beam travels from the inlet of the rotating deflection unit to the isocenter in the case where the gantry angle is the gantry reference angle, in that a second phase advance is defined as a change in a phase, of the phase space distribution of the charged particle beam, that changes when the charged particle beam travels from the inlet of the rotating deflection unit to the isocenter in the case where the gantry angle is pivoted by 90° from the gantry reference angle, and in that the fixed transport unit control excitation amounts of the quadrupole electromagnets in such a way that a phase of the phase space distribution of the charged particle beam at the inlet of the rotating deflection unit coincides with a phase determined by a calculation based on an average value of the first phase advance and the second phase advance.

Advantage of the Invention

In the charged particle beam transport system according to the present invention, in the fixed transport unit, the phase space distribution of a charged particle beam at the inlet of the rotating deflection unit coincides with a predetermined phase space distribution, for example, the phase of which is determined by a calculation based on the average value of the first phase advance and the second phase advance; therefore, even for a beam having an extremely small x-direction emittance, at the inlet of the rotating deflection unit of the charged particle beam transport system, that is a characteristic of a slow-extraction method, a beam size having a low rotation dependency can be realized at the isocenter.

BRIEF DESCRIPTION OF THE DRAWINGS

FIG. 4 is a side view of the rotating deflection unit in FIG. 3 when viewed from the left side;

FIG. 5A and FIG. 5B are graphs representing the betatron function of a charged particle over a section from the rotating deflection unit to an isocenter according to Embodiment 1 of the present invention;

MODES FOR CARRYING OUT THE INVENTION

Embodiment 1

Figure 1:
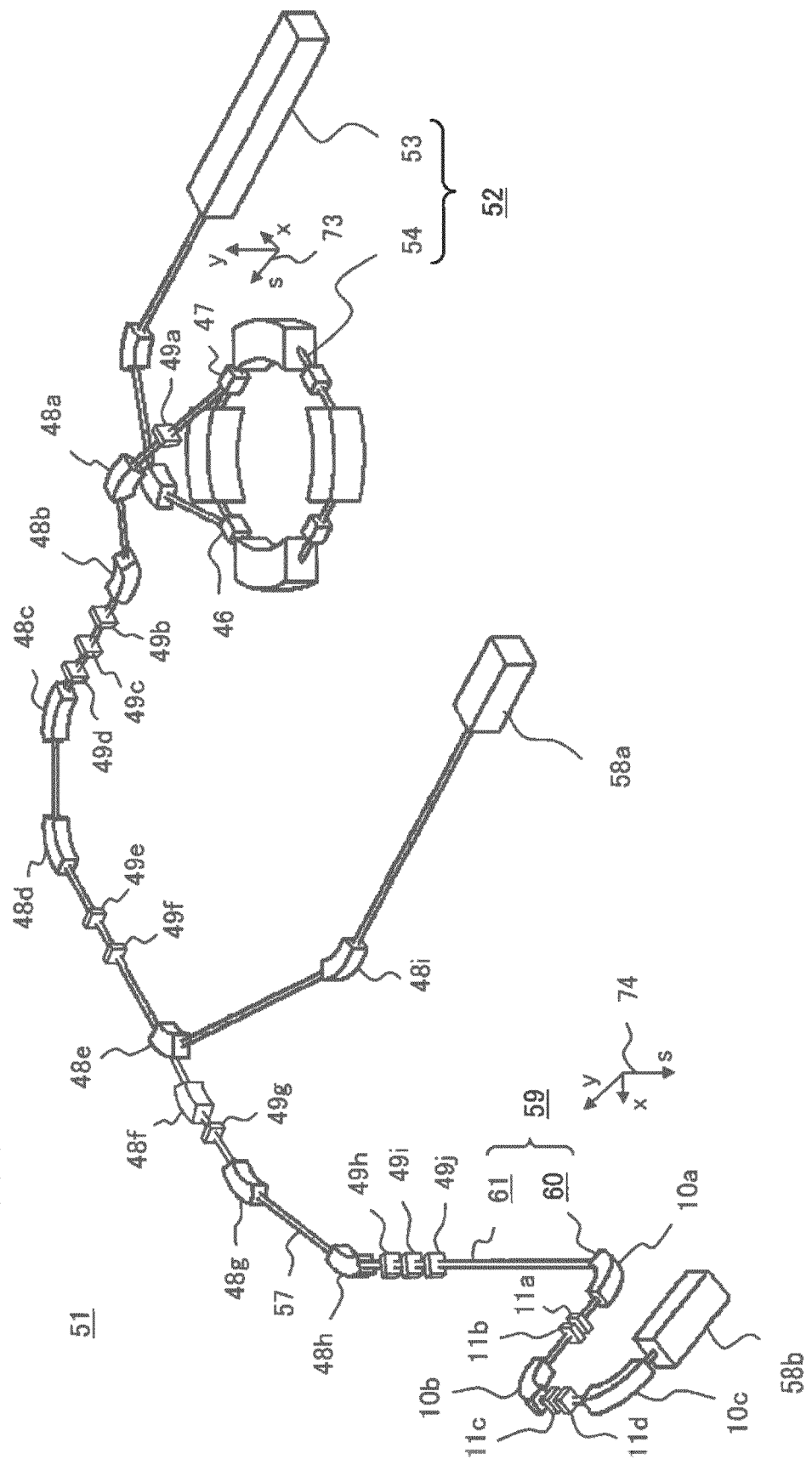
FIG. 1 is a schematic configuration diagram of a particle beam therapy system according to the present invention.
Figure 2:
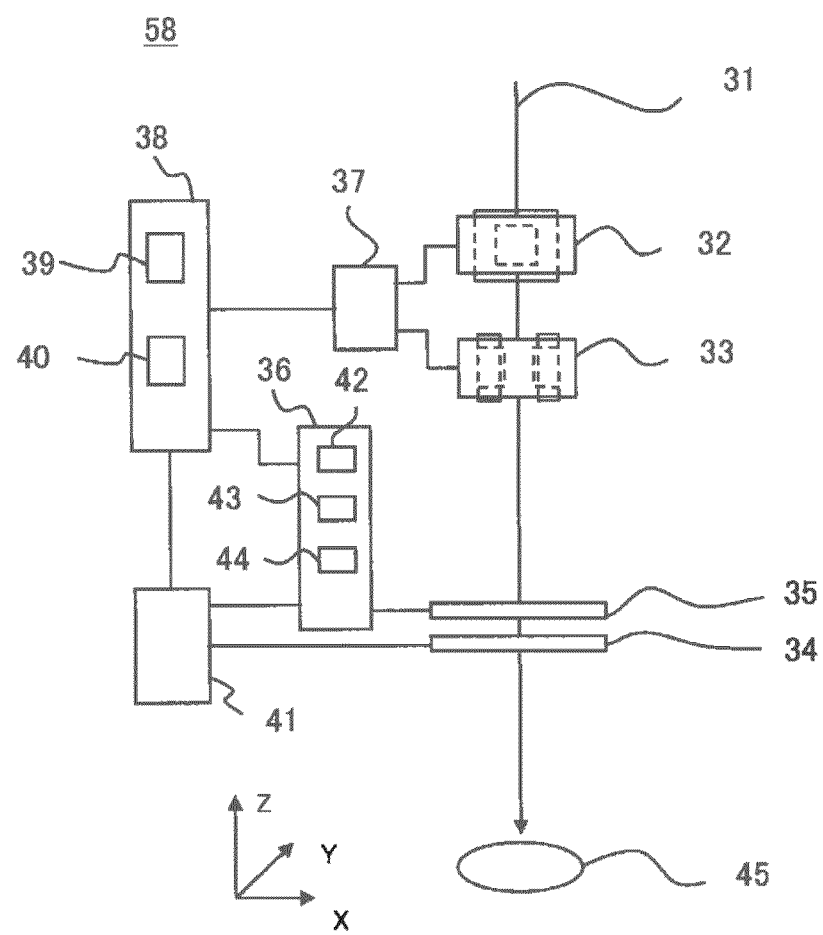
FIG. 2 is a diagram representing the configuration of the particle beam irradiation apparatus in FIG. 1.
Figure 3:
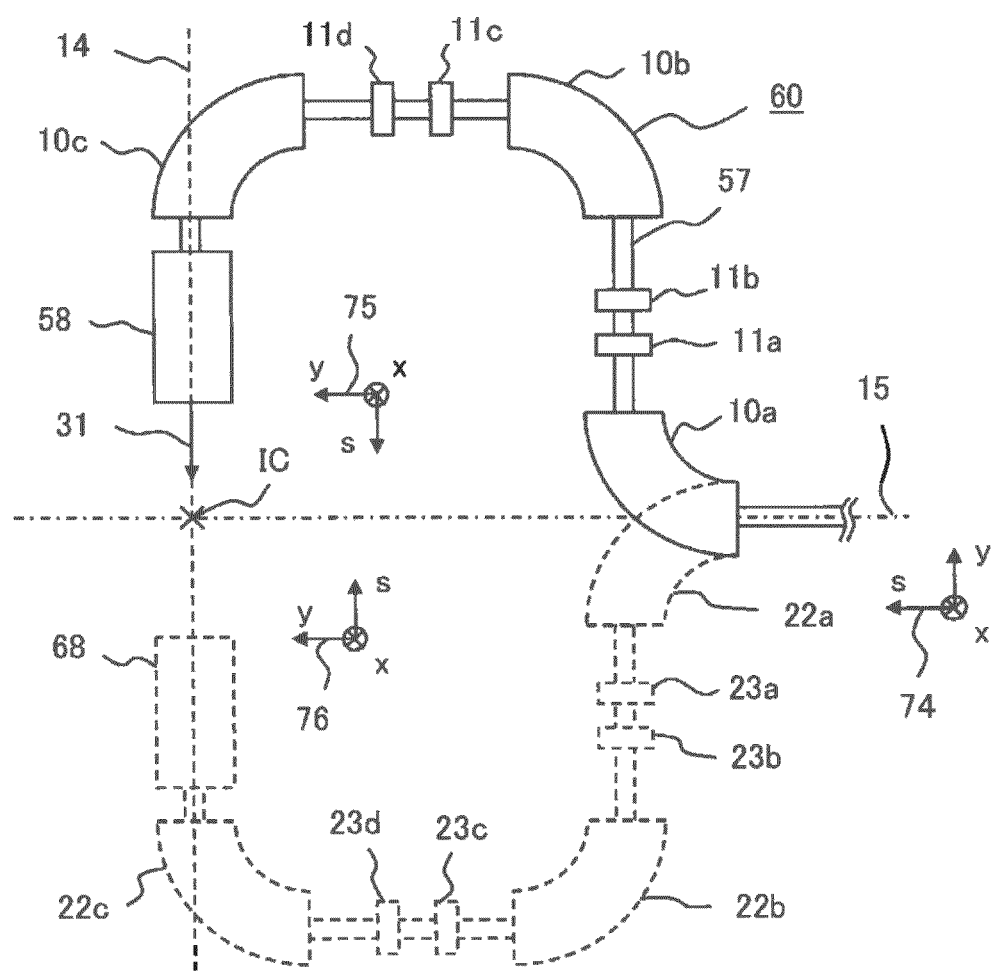
FIG. 3 is a diagram representing the configuration of a rotating deflection unit of a charged particle beam transport system according to the present invention.

FIG. 1 is a schematic configuration diagram of a particle beam therapy system according to the present invention; FIG. 2 is a diagram representing the configuration of a particle beam irradiation apparatus according to the present invention. FIG. 3 is a diagram representing the configuration of a rotating deflection unit of a charged particle beam transport system according to the present invention; FIG. 4 is a side view of the rotating deflection unit in FIG. 3 when viewed from the left side. In FIG. 1, a particle beam therapy system 51 includes a beam generation apparatus 52, a charged particle beam transport system 59, and particle beam irradiation apparatuses 58a and 58b. The beam generation apparatus 52 includes an ion source (unillustrated), a prestage accelerator 53, and an accelerator 54. The particle beam irradiation apparatus 58b is provided in a rotating gantry (unillustrated). The particle beam irradiation apparatus 58a is provided in a treatment room where no rotating gantry is installed.

The charged particle beam transport system 59 is to achieve communication between the accelerator 54 and the particle beam irradiation apparatuses 58a and 58b. The accelerator 54 and the particle beam irradiation apparatuses 58a and 58b are connected with each other by way of a vacuum duct 57; a charged particle beam passes through the vacuum duct 57. Part of the charged particle beam transport system 59 is provided in the rotating gantry (unillustrated), and a rotating deflection unit 60 provided in the rotating gantry includes a plurality of deflection electromagnets 10a, 10b, and 10c and a plurality of quadrupole electromagnets 11a, 11b, 11c, and 11d. The rotating deflection unit 60 rotates as the rotating gantry rotates. A fixed transport unit 61, which is other portion of the charged particle beam transport system 59 than the rotating deflection unit 60, includes a plurality of deflection electromagnets 48a, 48b, 48c, 48d, 48e, 48f, 48g, 48h, and 48i and a plurality of quadrupole electromagnets 49a, 49b, 49c, 49d, 49e, 49f, 49g, 49h, 49i, and 49j. As the reference numerals of the deflection electromagnets of the fixed transport unit 61, "48" is collectively utilized; however, in the case where the deflection electromagnets are separately explained, "48a" and "48i" are utilized. As the reference numerals of the quadrupole electromagnets of the fixed transport unit 61, "49" is collectively utilized; however, in the case where the quadrupole electromagnets are separately explained, "49a" and "49j" are utilized. As the reference numerals of the deflection electromagnets of the rotating deflection unit 60, "10" is collectively utilized; however, in the case where the deflection electromagnets are separately explained, "10a", "10b", and "10c" are utilized.

A charged particle beam, which is a particle beam such as a proton beam generated in the ion source, is accelerated by the prestage accelerator 53 and injected into the accelerator 54 through an injector 46. In this Description, the accelerator 54 will be explained with a synchrotron as an example. The particle beam is accelerated to gain predetermined energy. The charged particle beam launched from a launching apparatus 47 of the accelerator 54 is transported to the particle beam irradiation apparatuses 58a and 58b by way of the charged particle beam transport system 59. The particle beam irradiation apparatuses 58a and 58b each irradiate the charged particle beam onto an irradiation subject 45 (refer to FIG. 2). As the reference numerals of the particle beam irradiation apparatuses, "58" is collectively utilized; however, in the case where the particle beam irradiation apparatuses are separately explained, "58a" and "58b" are utilized. Letting x-direction denote a direction on the circular orbit plane of the accelerator 54 in a plane perpendicular to the traveling direction (the s-direction) of a charged particle beam 31 at the launching position of the accelerator 54 and y-direction denote a direction perpendicular to x-direction in a plane perpendicular to the traveling direction of the charged particle beam 31, the charged particle beam 31 launched from the accelerator 54 becomes a charged particle beam whose x-direction emittance is small and whose y-direction emittance is large. The beam coordinate system of the charged particle beam 31 at the launching position of the accelerator 54 is a beam coordinate system 73. The beam coordinate system of the charged particle beam 31 at the inlet of the rotating deflection unit 60 of the charged particle beam transport system 59 is a beam coordinate system 74. The s-direction axis, the x-direction axis, and the y-direction axis of the beam coordinate system will be referred to as the s axis, the x axis, and the y axis, respectively.

The charged particle beam 31 generated in the beam generation apparatus 52 and accelerated to gain predetermined energy is led to the particle beam irradiation apparatus 58 by way of the charged particle beam transport system 59. In FIG. 2, the particle beam irradiation apparatus 58 is provided with X-direction and Y-direction scanning electromagnets 32 and 33 that scan the charged particle beam 31 in X direction and Y direction, respectively, which are directions perpendicular to the charged particle beam 31; a position monitor 34; a dose monitor 35; a dose data converter 36; a beam data processing apparatus 41; a scanning electromagnet power source 37; and an irradiation management apparatus 38 that controls the particle beam irradiation apparatus 58. The irradiation management apparatus 38 is provided with an irradiation control computer 39 and an irradiation control apparatus 40. The dose data converter 36 is provided with a trigger generation unit 42, a spot counter 43, and an inter-spot counter 44. The traveling direction of the charged particle beam 31 is −Z direction.

The X-direction and Y-direction scanning electromagnets 32 and 33 scan the charged particle beam 31 in the X direction and the Y direction, respectively. The position monitor 34 detects beam information for calculating the passing position (gravity center position) through which the charged particle beam 31 that has been scanned by the X-direction scanning electromagnet 32 and the Y-direction scanning electromagnet 33 passes and the size of the charged particle beam 31. The beam data processing device 41 calculates the passing position (gravity center position) and the size of the charged particle beam 31, based on beam information including a plurality of analogue signals (beam information items) detected by the position monitor 34. Moreover, the beam data processing device 41 generates an abnormality detection signal indicating a positional abnormality or a dimensional abnormality of the charged particle beam 31 and outputs the abnormality detection signal to the irradiation management apparatus 38.

The dose monitor 35 detects the dose of the charged particle beam 31. The irradiation management apparatus 38 controls the irradiation position of the charged particle beam 31 on the irradiation subject 45, based on treatment plan data created by an unillustrated treatment planning apparatus; when the dose measured by the dose monitor 35 and converted into digital data by the dose data converter 36 reaches a desired dose, the charged particle beam 31 is stopped. The scanning electromagnet power source 37 changes setting currents for the X-direction scanning electromagnet 32 and the Y-direction scanning electromagnet 33, based on control inputs (commands), which are outputted from the irradiation management apparatus 38, to the X-direction scanning electromagnet 32 and the Y-direction scanning electromagnet 33.

In this Description, the scanning irradiation method of the particle beam irradiation apparatus 58 will be explained as the hybrid scanning irradiation method (a method in which when the beam irradiation position (spot) is changed, the beam is not stopped); specifically, it is explained as a method in which when the irradiation position of the charge particle beam 31 is changed, as is the case with the raster-scanning irradiation method, the charged particle beam 31 is not stopped and as is the case with the spot scanning irradiation method, the beam irradiation position travels through spot positions one after another. The spot counter 43 measures the irradiation dose for a time during which the beam irradiation position of the charged particle beam 31 is stopped. The inter-spot counter 44 measures the irradiation dose for a time during which the beam irradiation position of the charged particle beam 31 moves. The trigger generation unit 42 generates a dose completion signal when the dose of the charged particle beam 31 at the beam irradiation position reaches the desired irradiation position.

FIG. 3 illustrates the rotating deflection unit 60 of the charged particle beam transport system 59 at a time when the rotation angle (hereinafter, referred to also as a gantry angle, as may be necessary) at which the rotating deflection unit 60 rotates around a gantry rotation axle 15 is 0° or 180°. The drawing illustrated by a solid line is the rotating deflection unit 60 at a time when the rotation angle is 0°; the drawing illustrated by a broken line is the rotating deflection unit 60 at a time when the rotation angle is 180°. Different reference characters are provided to the drawing illustrated by the broken line in order to distinguish the drawing illustrated by the broken line from the drawing illustrated by the solid line. In the rotating deflection unit 60, the charged particle beam 31 passes through the electromagnets in the following order and then reaches the particle beam irradiation apparatus 58. The charged particle beam 31 passes through the deflection electromagnet 10a, the quadrupole electromagnets 11a and 11b, the deflection electromagnet 10b, the quadrupole electromagnet 11c and 11d, and the deflection electromagnet 10c, in that order. In the rotating deflection unit 60 at a time when the rotation angle is 180°, the charged particle beam 31 passes through the electromagnets in the following order and then reaches the particle beam irradiation apparatus 68 (FIGS. 3 and 4). Reference numerals different from 58 are also utilized for the particle beam irradiation apparatuses in FIGS. 3 and 4 in order to distinguish rotation angles from one another. The reference numerals of the particle beam irradiation apparatuses at a time when the rotation angles are 90°, 180°, and 270° are 67, 68, and 69, respectively. The charged particle beam 31 passes through the deflection electromagnet 22a, the quadrupole electromagnets 23a and 23b, the deflection electromagnet 22b, the quadrupole electromagnet 23c and 23d, and the deflection electromagnet 22c, in that order. An isocenter IC is a point at which beam center lines 14 intersect one another when the rotating deflection unit 60 rotates. The beam coordinate systems of the charged particle beam that has passed the particle beam irradiation apparatus at a time when the rotation angles are 0°, 90°, 180°, and 270° are beam coordinate systems 75, 77, 76, and 78, respectively.

In this situation, the reference of the gantry angle will be considered. It is defined that the gantry angle, which is the rotation angle at which the rotating deflection unit 60 rotates around the gantry rotation axle 15, is the angle between the beam center line 14 of the charged particle beam 31 in the particle beam irradiation apparatus 58 and the y-direction axis in the beam coordinate system 74 of the charged particle beam 31 at the inlet of the rotating deflection unit 60. It is defined that the gantry angle at a time when the beam center line 14 and the y-direction axis (y axis) of the charged particle beam 31 at the inlet of the rotating deflection unit 60 coincide with each other is the gantry reference angle. In the case where the gantry angle is the gantry reference angle, the charged particle beam 31 is transported by the charged particle beam transport system 59 in such a way that the x-direction and y-direction emittances at the launching position of the accelerator 54 are separated and the respective emittances are maintained. The gantry reference angle may be an arbitrary gantry angle; however, in this Description, it is defined that the gantry reference angle is 0°.

FIG. 4 is a side view of the rotating deflection unit in FIG. 3 when viewed from the left side; the respective side views at times when the rotation angles are 90° and 270° are added thereto. A beam center line 16 is obtained by rotating by 90° the beam center line 14 that passes through the particle beam irradiation apparatus 58 at a time when the rotation angle is 0° and the particle beam irradiation apparatus 68 at a time when the rotation angle is 180°; the beam center line 16 is the beam center line of the charged particle beam 31 that passes through the particle beam irradiation apparatus 67 at a time when the rotation angle is 90° and the particle beam irradiation apparatus 69 at a time when the rotation angle is 270°. In FIG. 4, the reference characters of the deflection electromagnets 10*a* and 10*c* at a time when the rotation angle is 0° are changed when the revolution angle is 90° or 270°. When the rotation angle is 90°, the reference characters of the deflection electromagnets are 20*a* and 20*c*; when the rotation angle is 270°, the reference characters of the deflection electromagnets are 24*a* and 24*c*.

The beam designing for the charged particle beam transport system 59 is to determine the arrangement of the deflection electromagnets and the quadrupole electromagnets and to adjust the respective strengths of the quadrupole electromagnets, i.e., to determine the transport matrix represented by the equation (1) below.

$$\begin{bmatrix} x_2 \\ x'_2 \\ y_2 \\ y'_2 \\ t_2 \\ p_{t_2} \end{bmatrix} = \begin{bmatrix} m_{11} & m_{12} & m_{13} & m_{14} & m_{15} & m_{16} \\ m_{21} & m_{22} & m_{23} & m_{24} & m_{25} & m_{26} \\ m_{31} & m_{32} & m_{33} & m_{34} & m_{35} & m_{36} \\ m_{41} & m_{42} & m_{43} & m_{44} & m_{45} & m_{46} \\ m_{51} & m_{52} & m_{53} & m_{54} & m_{55} & m_{56} \\ m_{61} & m_{62} & m_{63} & m_{64} & m_{65} & m_{66} \end{bmatrix} \begin{bmatrix} x_1 \\ x'_1 \\ y_1 \\ y'_1 \\ t_1 \\ p_{t_1} \end{bmatrix} \quad (1)$$

The beam designing of the rotating deflection unit 60 of the charged particle beam transport system 59 and the fixed transport unit 61 is similar to the beam designing of the charged particle beam transport system 59. The beam designing will be explained with the rotating deflection unit 60 of the charged particle beam transport system 59, as an example. The transport matrix represents the relationship between the three-dimensional coordinates and the momentum at the inlet and the three-dimensional coordinates and the momentum at the outlet. The element $(x_1, y_1, x'_1, y'_1, t_1, p_{t_1})$ in the right-hand side signifies the position $(x_1, y_1)$ of a charged particle at the inlet of the rotating gantry, the s-direction gradient $(x'_1, y'_1)$ thereof, the time $t_1$, and the momentum $p_{t_1}$ of the charged particle. The element $(x_2, y_2, x'_2, t_2, t_2, p_{t_2})$ in the left-hand side signifies the position $(x_2, y_2)$ of the charged particle at the outlet of the rotating deflection unit 60, the s-direction gradient $(x'_2, y'_2)$ thereof, the time $t_2$, and the momentum $p_{t_2}$ of the charged particle. The prime ['] denotes a differential by s, i.e., d/ds.

In the beam designing for the rotating deflection unit 60 of the charged particle beam transport system 59, the subject is to determine the foregoing transport matrix by a few number of magnets and parameters; to date, a betatron function β and a momentum dispersion function η, obtained by modifying the foregoing transport matrix, have been utilized. The momentum dispersion function η is Δpt/pt. In the present invention, assuming that as is the case with the conventional method, a beam characterized by the conditions "$η_x=0, η'_x=0, η_y=0$, and $η'_y=0$" appears at the inlet of the rotating deflection unit 60, the momentum dispersion function η is designed in such a way that at the outlet of the rotating deflection unit 60, the conditions "$η_x=0, η'_x=0, η_y=0$, and $η'_y=0$" are satisfied. When this restriction is imposed, it is only necessary to consider only the equation (2) below in the beam designing for the rotating deflection unit 60.

$$\begin{bmatrix} x_2 \\ x'_2 \\ y_2 \\ y'_2 \end{bmatrix} = \begin{bmatrix} m_{11} & m_{12} & m_{13} & m_{14} & m_{15} & m_{16} \\ m_{21} & m_{22} & m_{23} & m_{24} & m_{25} & m_{26} \\ m_{31} & m_{32} & m_{33} & m_{34} & m_{35} & m_{36} \\ m_{41} & m_{42} & m_{43} & m_{44} & m_{45} & m_{46} \end{bmatrix} \begin{bmatrix} x_1 \\ x'_1 \\ y_1 \\ y'_1 \end{bmatrix} \quad (2)$$

In the equation (2), the times $t_1$ and $t_2$ and the momentums $p_{t_1}$ and $p_{t_2}$ of a charged particle are not utilized; therefore, even when the rotating deflection unit 60 rotates as the gantry rotates, the difference in the momentum causes no change in the beam size and no difference in the beam size changing rate at the outlet of the rotating deflection unit 60.

Next, attention will be paid to the case where the gantry angle is 0° (or 180°) and the case where the gantry angle is 90° (or 270°). In the case where the deflection electromagnets of the rotating deflection unit 60 include only vertical deflection electromagnets or only horizontal deflection electromagnets, the equation (2) is modified to the equation (3), and hence the coupling between x direction and y direction is cancelled.

$$\begin{bmatrix} x_2 \\ x'_2 \\ y_2 \\ y'_2 \end{bmatrix} = \begin{bmatrix} m_{11} & m_{12} & 0 & 0 \\ m_{21} & m_{22} & 0 & 0 \\ 0 & 0 & m_{33} & m_{34} \\ 0 & 0 & m_{43} & m_{44} \end{bmatrix} \begin{bmatrix} x_1 \\ x'_1 \\ y_1 \\ y'_1 \end{bmatrix} \quad (3)$$

Moreover, at the inlet of the rotating deflection unit 60, the x-direction and y-direction values of each of the betatron functions β and α, which are characteristic amounts in the beam phase space, are made to coincide with each other, i.e., the conditions "$β_x=β_y$, and $α_x=α_y$," are satisfied, so that the difference in the betatron function β causes no rotation dependency of the beam size. The functions β and α with respect to "s" are each referred to as a betatron function.

In the beam designing for the rotating deflection unit 60 according to Embodiment 1, the conditions at the inlet and outlet of the rotating deflection unit 60 are established as follows:

The conditions at the inlet of the rotating deflection unit 60 are $β_x=β_y, α_x=α_y, η_x=0, η'_x=0, η_y=0$, and $η'_y=0$.

The conditions at the outlet of the rotating deflection unit 60 are $β_x=β_y, α_x=α_y, η_x=0, η'_x=0, η_y=0$, and $η'_y=0$.

By establishing the conditions at the inlet and outlet of the rotating deflection unit 60 in such a way as described above, i.e., by simplifying the conditions as much as possible, the beam designing for the rotating deflection unit 60 can be implemented with a few number of adjustment parameters. The adjustment parameters in the equation (3) are $m_{11}, m_{12}, m_{21}, m_{22}, m_{33}, m_{34}, m_{43}$, and $m_{44}$.

Figure 6A:
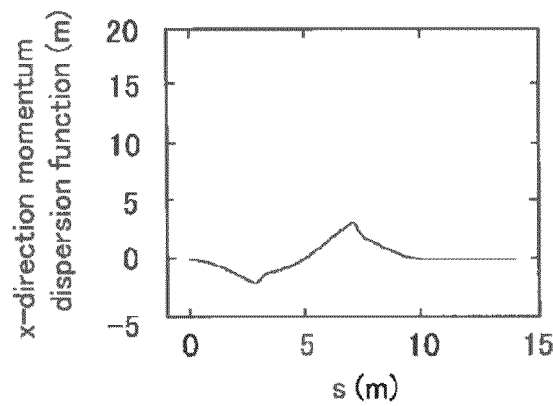
FIG. 6A and FIG. 6B are graphs representing the momentum dispersion function of a charged particle over a section from the rotating deflection unit to an isocenter according to Embodiment 1 of the present invention.
Figure 6B:
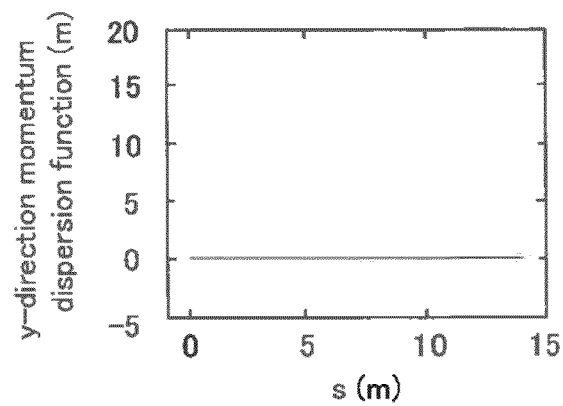

FIGS. 5A, 5B and 6A, 6B represent the betatron function β and the momentum dispersion function η, respectively, of the rotating deflection unit 60 in FIG. 3. FIG. 5A and FIG. 5B are graphs representing the betatron function of a charged particle over a section from the rotating deflection unit to an isocenter IC according to Embodiment 1 of the present invention. The abscissa denotes the s-direction distance; the ordinate denotes the betatron function β. In FIG. 5A and FIG. 5B, the betatron function α is not represented. FIG. 5A represents the x-direction betatron function β; FIG. 5B represents the y-direction betatron function β. FIG. 6A and FIG. 6B are graphs representing the momentum dispersion function of a charged particle over a section from the rotating deflection unit to an isocenter IC according to Embodiment 1 of the present invention. The abscissa denotes the s-direction distance; the ordinate denotes the momentum dispersion function η. FIG. 6A represents the x-direction momentum dispersion function η; FIG. 6B represents the y-direction momentum dispersion function η. In each of FIGS. 5A, 5B, 6A, and 6B, the inlet of the rotating deflection unit 60 is at s=0 m, and the outlet of the rotation deflection unit 60 is approximately at s=14 m, i.e., the right end. In Embodiment 1, the four quadrupole electromagnets 11a, 11b, 11c, and 11d realizes a transport matrix in which the charged particle beam 31 passes through the rotating deflection unit 60 and the beam characteristics at the isocenter IC become excellent.

In the case of a conventional irradiation method other than the scanning irradiation method, even when the x-direction and y-direction beam sizes at the isocenter IC are different from each other, the difference does not pose a substantial problem, because in an actual irradiation, the scatterer and the Wobbler electromagnet enlarge the beam size and the charged particle is irradiated after being scattered at the outlet of the rotating deflection unit, to the extent that the beam size thereof does not depend on the initial beam size. However, in the scanning irradiation method, it is required that the beam size is as small as possible; thus, it is desired that the scatter is as little as possible. In the case where it is desired that the scatter is as little as possible, it is preferable that in the beam designing for the accelerator 54 and the charged particle beam transport system 59, the x-direction and y-direction beam sizes are approximately the same and do not have the dependency on the angle of the rotating gantry.

Figure 7A:
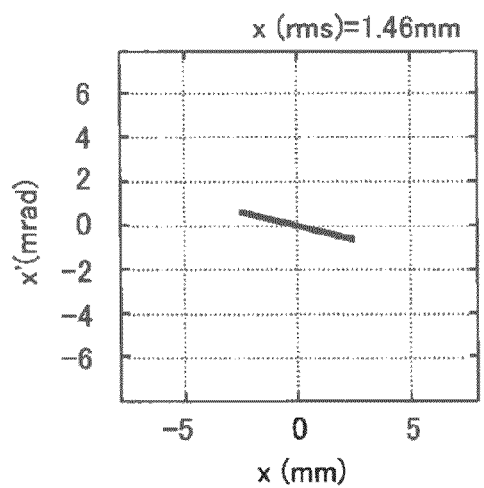
FIG. 7A and FIG. 7B are graphs representing the phase space distribution of a charged particle at the inlet of the rotating deflection unit according to Embodiment 1 of the present invention.
Figure 7B:
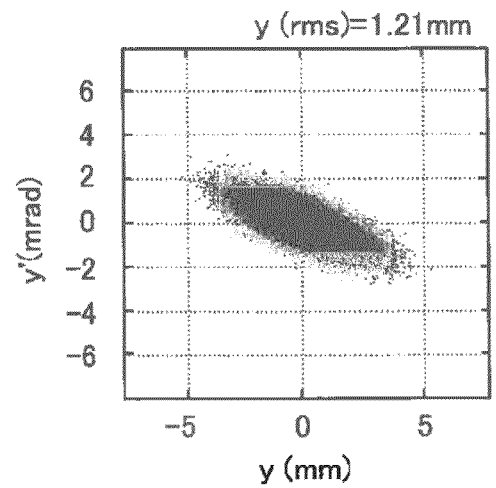

In general, an x-direction beam size $\sigma_x$ and a y-direction beam size $\sigma_y$ are expressed as represented by the equation (4). The elements $\epsilon_x$ and $\epsilon_y$ are the x-direction emittance and the y-direction emittance, respectively. The emittances $\epsilon_x$ and $\epsilon_y$ are areas in the phase space. The x-direction phase space is expressed as represented in FIG. 7A; it is a space represented by the abscissa denoting the x-direction distance x and the ordinate denoting the x-direction gradient x'. Similarly, the y-direction phase space is expressed as represented in FIG. 7B; it is a space represented by the abscissa denoting the y-direction distance y and the ordinate denoting the y-direction gradient y'.

$$\sigma_x = \sqrt{\beta_x \epsilon_x}$$

$$\sigma_y = \sqrt{\beta_y \epsilon_y} \qquad (4)$$

The betatron functions $\beta_x$ and $\beta_y$ are quantities (depending on the transport matrix) that can be changed by the beam designing for the rotating gantry. In contrast, the emittances $\epsilon_x$ and $\epsilon_y$ are quantities that are determined by the launch from the accelerator 54; when in the charged particle beam transport system 59, there exists no scatterer or the like during the transport of a charged particle, the emittances $\epsilon_x$ and $\epsilon_y$ are constant. The emittances $\epsilon_x$ and $\epsilon_y$ depend on the mechanism of extracting a charged particle beam from the accelerator 54; when the charged beam is launched from the accelerator 54 based on a slow-extraction method, the values of the emittances $\epsilon_x$ and $\epsilon_y$ differ from each other. The emittance $\epsilon_y$ is much larger than the emittance $\epsilon_x$; the emittance $\epsilon_y$ is twice as large as the emittance $\epsilon_x$ to ten times larger than the emittance $\epsilon_x$. In the present invention, the difference in the beam size caused by the difference between the emittances $\epsilon_x$ and $\epsilon_y$ is reduced as much as possible by the beam designing for the charged particle beam transport system 59.

When in the rotating deflection unit 60, there exists a configuration in which a scatterer and a quadrupole electromagnet are combined with each other or when even though the number of quadrupole electromagnets of the rotating deflection unit 60 is small, the respective strengths of the quadrupole electromagnets are changed in accordance with the rotation angle of the rotating gantry, it is made possible to reduce the difference in the beam size as much as possible. However, it is important that by cancelling the difference in the beam size depending on the rotation angle, without changing the strength of the quadrupole electromagnet, so that the rotating deflection unit 60 can be realized at low cost. It is desirable that the foregoing beam designing method for the charged particle beam transport system 59 can be applied to an existing facility and the rotating deflection unit 60 of the charged particle beam transport system 59 can be realized also in the existing facility. As can be seen from the equation (3), the beam designing for the charged particle beam transport system 59 can be implemented with the 2-by-2 transport matrix with respect to x and x' and the 2-by-2 transport matrix with respect to y and y' separated from each other.

Next, the effect of a small emittance will be discussed. In the beam extraction method (slow beam extraction method) in which the charged particle beam 31 is slowly extracted from the accelerator 54, the charged particle beam 31 circulating in the accelerator 54 is moved to the outer circumference side (to x direction) of the accelerator 54, and only the outer-circumference portion of the charged particle beam 31 is extracted; thus, the circulating charged particle beam 31 is gradually launched little by little from the accelerator 54 into the charged particle beam transport system 59 over a long period. FIG. 7A and FIG. 7B are graphs representing the phase space distribution of a charged particle at the inlet of the rotating deflection unit according to Embodiment 1 of the present invention. FIG. 7A represents the x-direction phase space distribution; FIG. 7B represents the y-direction phase space distribution. Because the x-direction distribution is limited by the inherent characteristics of launch from the accelerator 54, the x-direction phase space distribution at the inlet of the rotating deflection unit 60 is not in a shape of an ellipse but approximately in a shape of a line. In contrast, because the y-direction distribution is not limited, the y-direction phase space distribution is in a shape of an ellipse. The area in the phase space is an emittance; therefore, the x-direction and y-direction emittances are much different from each other.

The beam designing for the charged particle beam transport system 59 according to Embodiment 1 of the present invention is divided into beam designing for the rotating deflection unit 60, with which the charged particle beam 31 passes through the rotating deflection unit 60 and the beam characteristics at the isocenter IC becomes excellent and into beam designing for the fixed transport unit 61, with which there is realized the phase space distribution, of a charged particle inputted to the rotating deflection unit 60, that realizes the beam size having a low rotation dependency at the isocenter IC. When the beam designing for the fixed transport unit 61 is implemented, there is determined the phase space distribution, of a charged particle inputted to the rotating deflection unit 60, that realizes the beam size having a low rotation dependency at the isocenter IC.

When the phase space distribution of a charged particle inputted to rotating deflection unit 60 is determined, the x-direction phase space distribution is made to approximate a line and the y-direction phase space distribution is made to approximate an ellipse. Because the x-direction phase space distribution is made to approximate a line, not the area but the phase thereof is important. The phase of the x-direction phase space distribution at the inlet of the rotating deflection unit 60 is determined while attention is paid to the phase relationship of the rotating gantry. Specifically, a phase $\phi_{ix}$ of the x-direction phase space distribution at the inlet of the rotating deflection unit 60 is determined through a calculation based on the average value of the respective phase advances over a section from the inlet to the outlet of the rotating deflection unit 60 at times when the gantry angles are $\theta_1$ and $\theta_2$ that are different by 90° from each other; for example, the phase $\phi_{ix}$ is obtained by adding a minus (−) sign to the average value of the respective decimal parts of the phase advances over a section from the inlet to the outlet at times the gantry angles are 0° and 90°.

There will be considered a case where by use of the transport matrix for the rotating deflection unit 60, the rotating deflection unit 60 is designed in such a way that when the electromagnet arrangement of the rotating deflection unit 60 is as illustrated in FIG. 3, the electromagnets have respective strengths for realizing the betatron function and the momentum dispersion function represented in FIGS. 5A, 5B and 6A, 6B, respectively. The phase advance $\phi 1$ at a time when the gantry angle is 0° (when the rotating deflection unit 60 is arranged as illustrated by the solid line in FIG. 4) is 1.382 (497.52°); the phase space distribution is pivoted by 497.52° at the outlet of the rotating deflection unit 60. The phase advance $\phi 2$ at a time when the gantry angle is 90° (when the rotating deflection unit 60 is arranged as illustrated with deflection electromagnets 20a and 20c and the particle beam irradiation apparatus 67 in FIG. 4) is 0.522; the phase space distribution is pivoted by 93.96° at the outlet of the rotating deflection unit 60. The phase space distribution of the charged particle beam 31 at a time when the gantry angle is 180° theoretically coincides with the phase space distribution of the charged particle beam 31 at a time when the gantry angle is 0°. The gantry angle 360° means one round, i.e., twice as large as 180°; thus, neglecting the one-round phase advance, i.e., performing normalization with 180° phase advance, it is assumed that the phase advance $\phi 1$ is 137.52° (=497.52°−360°).

In order to prevent a change in the gantry angle from changing the x-direction beam size, there is utilized 114.465° that is an intermediate value (average value) between 93.96°, which is the phase advance $\phi 2$, and 137.52°, which is the phase advance $\phi 1$. In other words, by setting the phase of the x-direction phase space distribution at the inlet of the rotating deflection unit 60 to −114.465°, approximately the same beam size can be realized at the outlet of the rotating deflection unit 60 and at the isocenter IC, regardless of whether as represented in FIGS. 8A, 8B and 11A, 11B, the gantry angle of the rotating deflection unit 60, i.e., the setting angle of the rotating gantry is 0° or 90°. The reason why the minus (−) sign is added to the average value will be described later.

When the charged particle beam 31 is scanned by neither the X-direction scanning electromagnet 32 nor the Y-direction scanning electromagnet 33, the beam size at the isocenter IC is approximately the same as the beam size at the outlet of the rotating deflection unit 60. When the charged particle beam 31 is scanned by the X-direction scanning electromagnet 32 and the Y-direction scanning electromagnet 33, the beam size at the isocenter IC slightly changes, in comparison with the case where the charged particle beam 31 is not scanned; however, even in this case, the beam size at the isocenter IC is approximately the same as the beam size at the outlet of the rotating deflection unit 60.

FIGS. 8A, 8B through 15A, 15B are graphs representing the phase space distributions of a charged particle at an isocenter IC at times when the angles of the rotation deflection unit according to Embodiment 1 of the present invention are 0°, 30°, 60°, 90°, 120°, 150°, 180°, and 210°, respectively. The graph in each of FIGS. 8A through 15A represents the x-direction phase space distribution; the graph in each of FIGS. 8B through 15B represents the y-direction phase space distribution. In the graph in each of FIGS. 8A through 15A, the abscissa denotes the x-direction distance x, and the ordinate denotes the x-direction gradient x'. In the graph in each of FIGS. 8B through 15B, the abscissa denotes the y-direction distance y, and the ordinate denotes the y-direction gradient y'. The character "rms" denotes a root mean square. The beam size (rms) represented in each graph corresponds to the standard deviation $\sigma$. The beam size (rms) will be referred to as a beam size $1\sigma$.

Figure 8A:
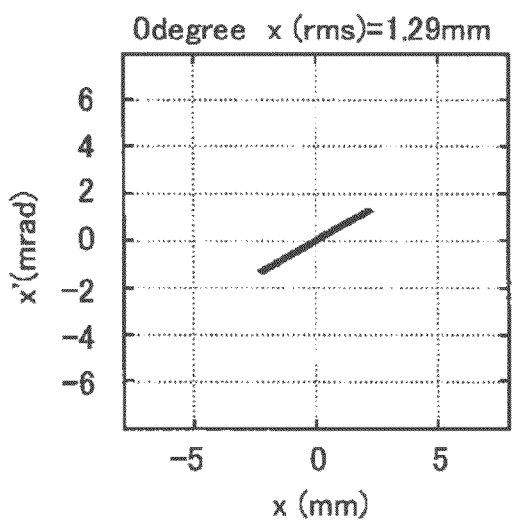
FIG. 8A and FIG. 8B are graphs representing the phase space distribution of a charged particle at an isocenter when the angle of the rotating deflection unit according to Embodiment 1 of the present invention is 0°.
Figure 8B:
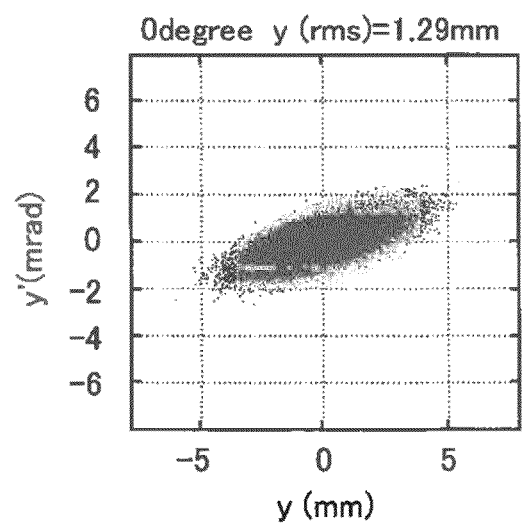
Figure 9A:
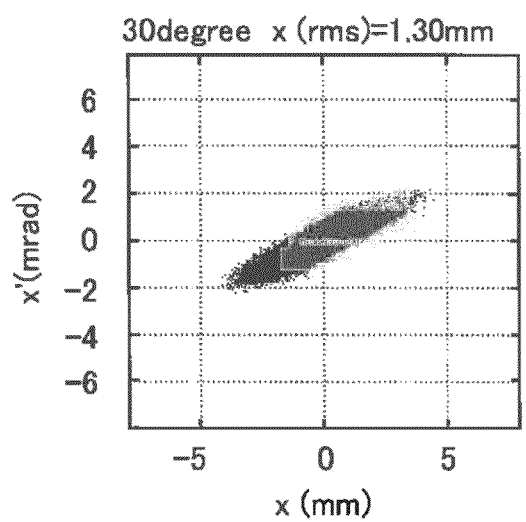
FIG. 9A and FIG. 9B are graphs representing the phase space distribution of a charged particle at an isocenter when the angle of the rotating deflection unit according to Embodiment 1 of the present invention is 30°.
Figure 9B:
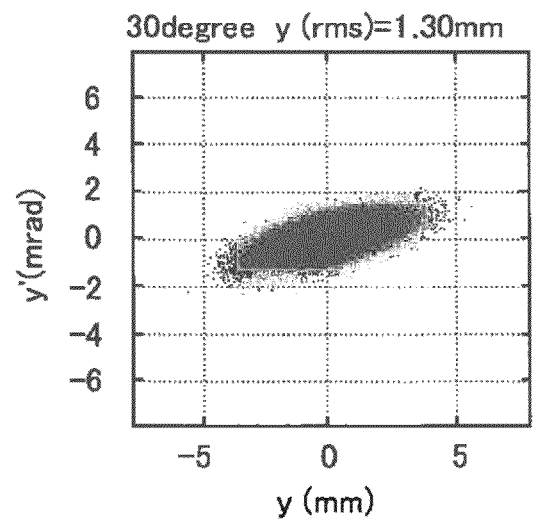
Figure 10A:
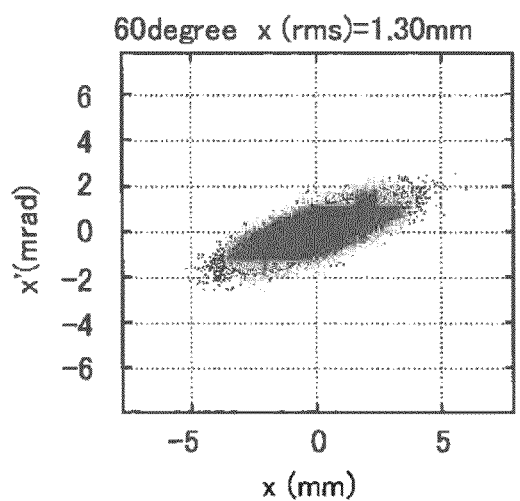
FIG. 10A and FIG. 10B are graphs representing the phase space distribution of a charged particle at an isocenter when the angle of the rotating deflection unit according to Embodiment 1 of the present invention is 60°.
Figure 10B:
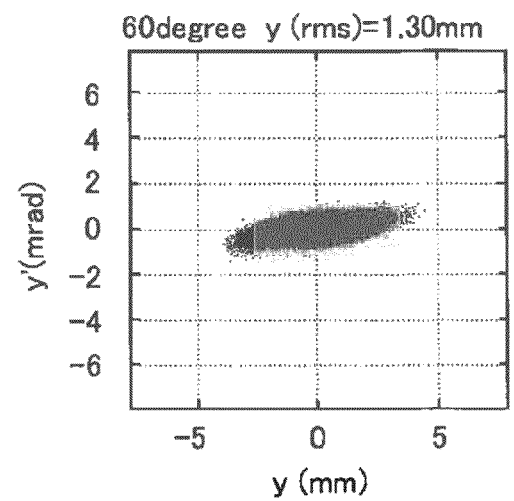
Figure 11A:
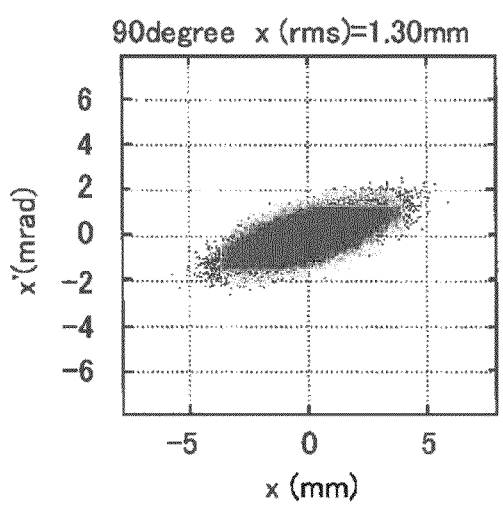
FIG. 11A and FIG. 11B are graphs representing the phase space distribution of a charged particle at an isocenter when the angle of the rotating deflection unit according to Embodiment 1 of the present invention is 90°.
Figure 11B:
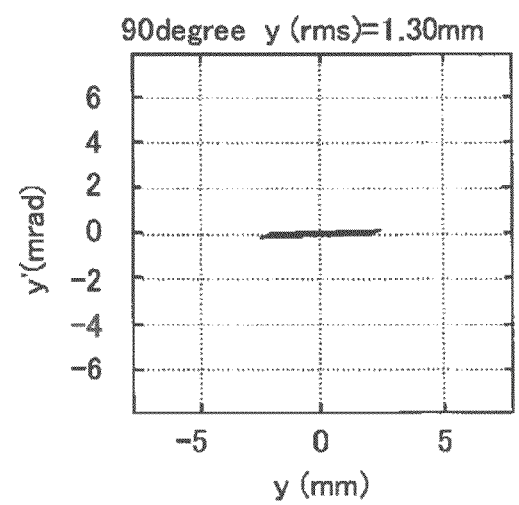

As represented in FIG. 8A and FIG. 8B, in the case where the angle of the rotating deflection unit 60 is 0°, the x-direction beam size $1\sigma$ and the y-direction beam size $1\sigma$ are 1.29 mm and 1.29 mm, respectively. As represented in FIG. 9A and FIG. 9B, in the case where the angle of the rotating deflection unit 60 is 30°, the x-direction beam size $1\sigma$ and the y-direction beam size $1\sigma$ are 1.30 mm and 1.30 mm, respectively. As represented in FIG. 10A and FIG. 10B, in the case where the angle of the rotating deflection unit 60 is 60°, the x-direction beam size $1\sigma$ and the y-direction beam size $1\sigma$ are 1.30 mm and 1.30 mm, respectively. As represented in FIG. 11A and FIG. 11B, in the case where the angle of the rotating deflection unit 60 is 90°, the x-direction beam size $1\sigma$ and the y-direction beam size $1\sigma$ are 1.30 mm and 1.30 mm, respectively.

Figure 12A:
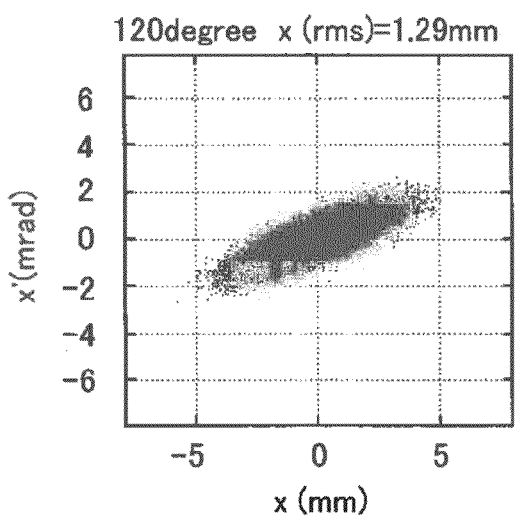
FIG. 12A and FIG. 12B are graphs representing the phase space distribution of a charged particle at an isocenter when the angle of the rotating deflection unit according to Embodiment 1 of the present invention is 120°.
Figure 12B:
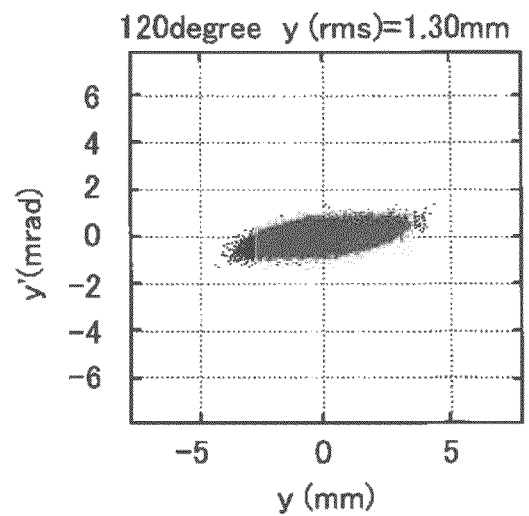
Figure 13A:
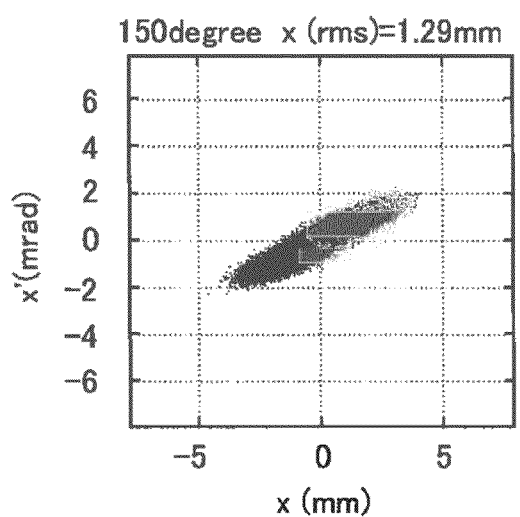
FIG. 13A and FIG. 13B are graphs representing the phase space distribution of a charged particle at an isocenter when the angle of the rotating deflection unit according to Embodiment 1 of the present invention is 150°.
Figure 13B:
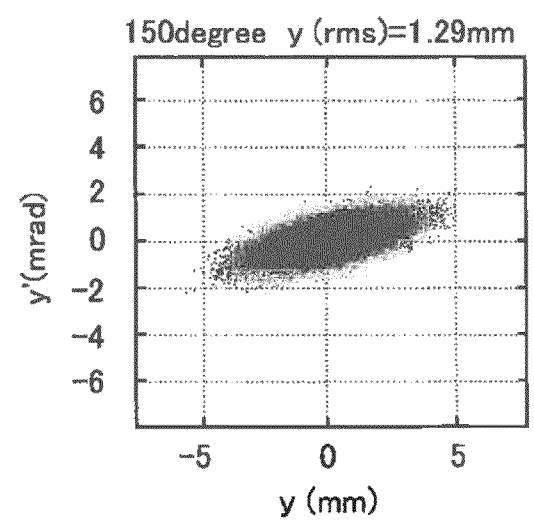
Figure 14A:
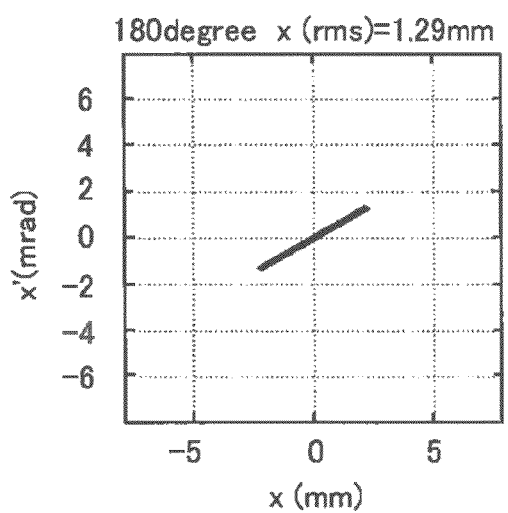
FIG. 14A and FIG. 14B are graphs representing the phase space distribution of a charged particle at an isocenter when the angle of the rotating deflection unit according to Embodiment 1 of the present invention is 180°.
Figure 14B:
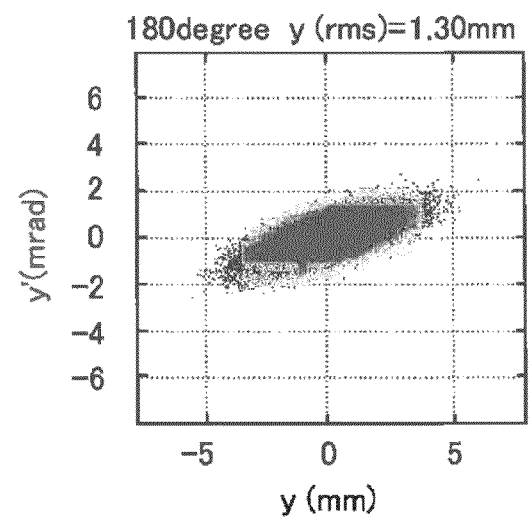
Figure 15A:
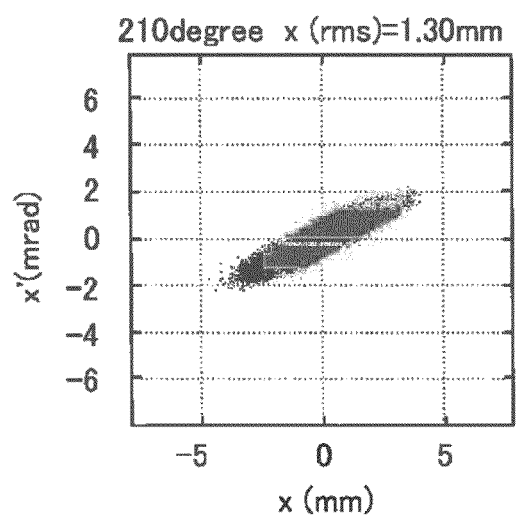
FIG. 15A and FIG. 15B are graphs representing the phase space distribution of a charged particle at an isocenter when the angle of the rotating deflection unit according to Embodiment 1 of the present invention is 210°.
Figure 15B:
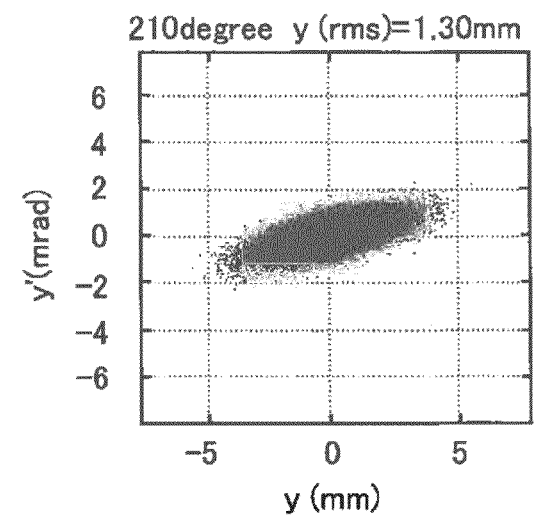

As represented in FIG. 12A and FIG. 12B, in the case where the angle of the rotating deflection unit is 120°, the x-direction beam size $1\sigma$ and the y-direction beam size $1\sigma$ are 1.29 mm and 1.30 mm, respectively. As represented in FIG. 13A and FIG. 13B, in the case where the angle of the rotating deflection unit is 150°, the x-direction beam size $1\sigma$ and the y-direction beam size $1\sigma$ are 1.29 mm and 1.29 mm, respectively. As represented in FIG. 14A and FIG. 14B, in the case where the angle of the rotating deflection unit is 180°, the x-direction beam size $1\sigma$ and the y-direction beam size $1\sigma$ are 1.29 mm and 1.30 mm, respectively. As represented in FIG. 15A and FIG. 15B, in the case where the angle of the rotating deflection unit is 210°, the x-direction beam size $1\sigma$ and the y-direction beam size $1\sigma$ are 1.30 mm and 1.30 mm, respectively.

As represented in each of FIGS. 8A, 8B through 15A, 15B, although the shapes and phases of the x-direction and y-direction phase space distributions are different from each other, the x-direction beam size $1\sigma$ and the y-direction beam size $1\sigma$ are approximately the same as each other. The reason why the minus (−) sign is added to the average value of the phase advances $\phi 1$ and $\phi 2$ will be described. The selection of the phase at the inlet of the rotating deflection unit 60 is important. In the case where the way of selecting the phase at the inlet is wrong, the phase space distribution of a beam becomes perpendicular in the phase space at the outlet; therefore, the beam size becomes so small that the desired beam size cannot be realized; thus, wrong selection of the phase is not preferable. The reason why the minus (−) sign is added to the average value of the phase advances $\phi 1$ and $\phi 2$ is that the phase advance in the gantry is cancelled at the outlet (isocenter) of the rotating deflection unit 60. Because the phase advances over a section from the inlet to the outlet of the rotating gantry, it is desirable that the phase at the inlet is shifted backward by the phase by which the phase space distribution advances. For example, when it is assumed that the phase advances by 60° in the rotating gantry and the phase at the inlet is set to −60°, the phase advance in the rotating deflection unit 60 is cancelled at the outlet (isocenter) of the outlet of the rotating deflection unit 60.

Figure 16:
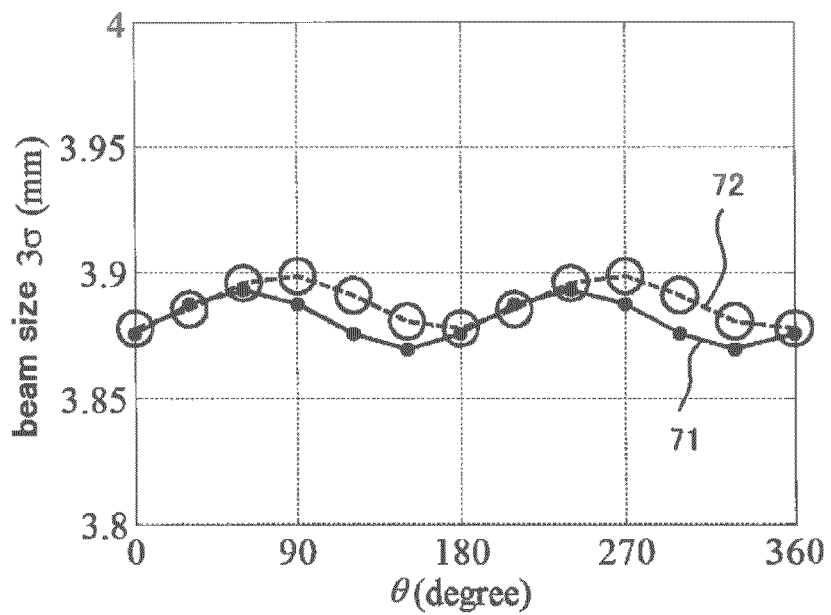
FIG. 16 is a graph representing the relationship between the beam size at an isocenter and the angle of the rotating deflection unit according to Embodiment 1 of the present invention.

FIG. 16 is a graph representing the relationship between the beam size at the isocenter IC and the angle of the rotating deflection unit according to Embodiment 1 of the present invention. The abscissa denotes the gantry angle θ of the rotating deflection unit 60, and the ordinate denotes the beam size 3σ that is thrice as large as the standard deviation σ. The characteristic 71 represented by a solid line is the x-direction characteristic, and the characteristic 72 represented by a broken line is the y-direction characteristic. When the rotating deflection unit 60 according to Embodiment 1 is configured in such a way as described above, there can be realized an approximately constant beam size that does not depend on the rotation angle of the rotating deflection unit 60, i.e., the rotation angle of the rotating gantry.

The charged particle beam transport system 59 according to Embodiment 1 is realized by use of the inlet conditions obtained by adding the phase $\phi_{ix}$ of the x-direction phase space distribution to the conditions "$\beta_x=\beta_y$, $\alpha_x=\alpha_y$, $\eta_x=0$, $\eta'_x=0$, $\eta_y=0$, and $\eta'_y=0$", which are the inlet conditions for the rotating deflection unit 60 according to a conventional designing method. The phase $\phi_{ix}$ of the x-direction phase space distribution at the inlet of the rotating deflection unit 60 is obtained by adding a minus (−) sign to the average value of the respective decimal parts of the phase advances over a section from the inlet to the outlet of the rotating deflection unit 60 at times when the gantry angles are $\theta_1$ and $\theta_2$ that are different by 90° from each other. In order to make the phase $\phi_{ix}$ of the x-direction phase space distribution at the inlet of the rotating deflection unit 60 coincide with a designed predetermined value, for example, a quadrupole electromagnet is added to the fixed transport unit 61 of the charged particle beam transport system 59, the positions of the quadrupole electromagnets are shifted, or the setting values of the excitation amounts are changed.

Next, there will be explained beam designing for the fixed transport unit 61 of the charged particle beam transport system 59 according to the present invention. The fixed transport unit 61 of the charged particle beam transport system 59 is designed in such a way as to satisfy the three conditions below. The condition 1 is that the charged particle beam 31 passes through the fixed transport unit 61. The condition 2 is that the momentum dispersion function η and the y-direction phase space distribution of a charged particle satisfy the conventional conditions. The condition 3 is that the x-direction phase space distribution of a charged particle at the inlet of the fixed transport unit 61 becomes a predetermined phase space distribution, inputted to the rotating deflection unit 60, that realizes the beam size having a low rotation dependency at the isocenter IC. The phase of the predetermined phase space distribution at the rotating deflection unit 60 of the charged particle beam transport system 59 according to Embodiment 1 is the foregoing phase $\phi_{ix}$ of the x-direction phase space distribution at the inlet of the rotating deflection unit 60; the phase $\phi_{ix}$ is obtained by adding a minus (−) sign to the average value of the respective decimal parts obtained by subtracting half-integer parts from the phase advances over a section from the inlet to the outlet of the rotating deflection unit 60 at times when the gantry angles are $\theta_1$ and $\theta_2$ that are different by 90° from each other.

In general, in beam physics, there is considered the motion of a particle in a phase space in which the abscissa is "x" and the ordinate is "xζ". As a beam travels, the particle distribution in the phase space contracts or expands in accordance with the betatron function (β(s)) and rotates in accordance with the phase advance. In the case where β is the same, the beam size depends on the phase of the particle distribution. For the purpose of paying attention only to the phase, there is considered a normalized phase space in which deformation due to the betatron function is normalized. In this normalized phase space, the range in which "x" can exist is ±1, and the range in which "x'" can exist is ±1.

In this normalized phase space, the size does not change, and the beam pivots counterclockwise each time it is transported. For example, it is assumed that the x-direction phase advance at a time when the angle of the rotating gantry is 0° is $\nu_0$ (=2.9) and the x-direction phase advance at a time when the angle of the rotating gantry is 90° is $\nu_{90}$ (=0.8). The concept of the phase calculation will be explained with reference to FIGS. 38 through 40.

Figure 38:
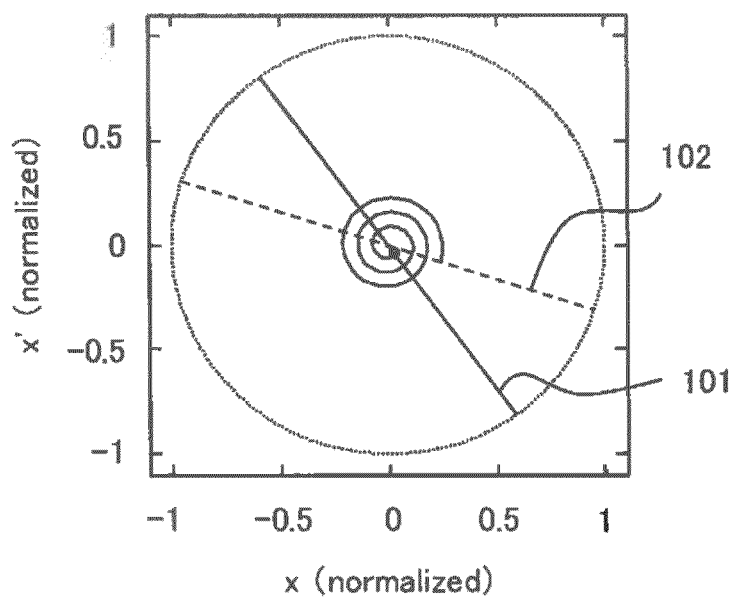
FIG. 38 is a chart of a normalized phase space for explaining the concept of a phase calculation.
Figure 39:
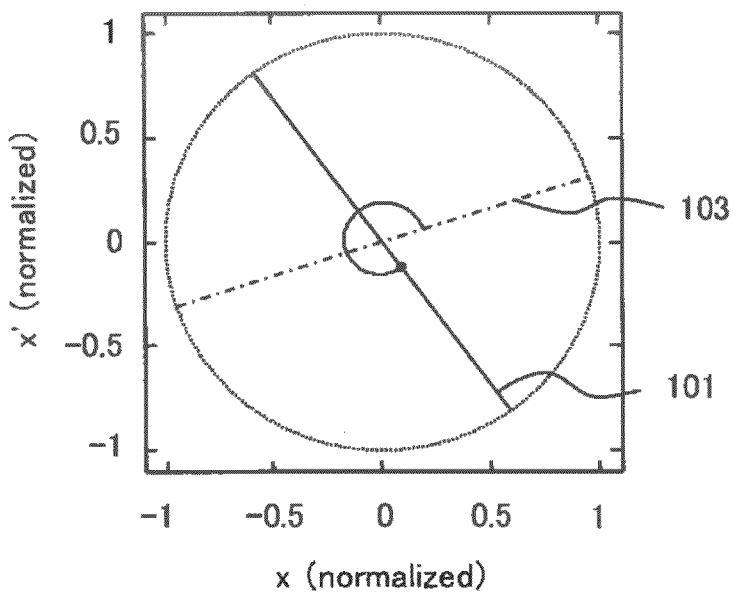
FIG. 39 is a chart of a normalized phase space for explaining the concept of a phase calculation.
Figure 40:
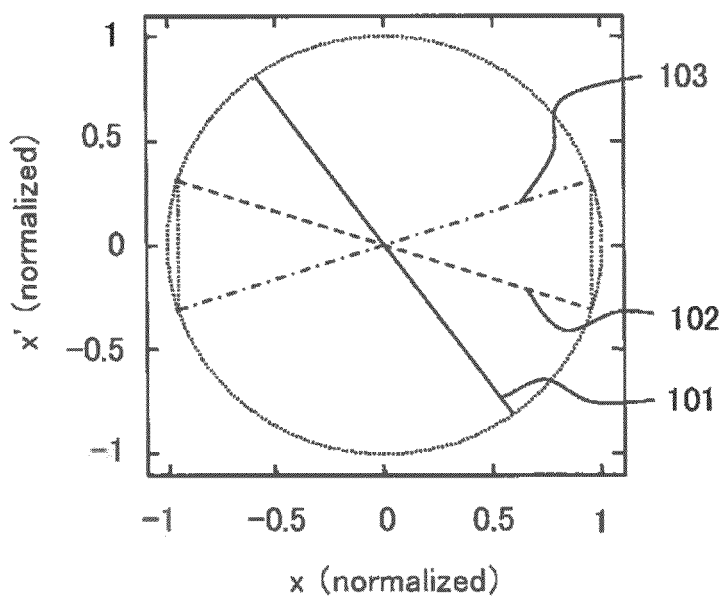
FIG. 40 is a chart of a normalized phase space for explaining the concept of a phase calculation.

FIG. 38 is the normalized phase space at a time when it is assumed that the phase at the inlet of the rotating gantry is 0.15 and the x-direction phase at a time when the angle of the rotating gantry is 0° advances to $\nu_0$ (=2.9). FIG. 39 is the normalized phase space at a time when it is assumed that the phase at the inlet of the rotating gantry is 0.15 and the x-direction phase at a time when the angle of the rotating gantry is 90° advances to $\nu_{90}$ (=0.8). FIG. 40 is a chart for comparing the case where the x-direction phase advance is $\nu_0$ (=2.9) and the case where the x-direction phase advance is $\nu_{90}$ (=0.8) under the assumption that the phase at the inlet of the rotating gantry is 0.15. In FIGS. 38 through 40, a phase line 101 denotes the phase at the inlet of the rotating gantry; a phase line 102 denotes the phase at the isocenter IC at a time when the angle of the rotating gantry is 0°; a phase line 103 denotes the phase at the isocenter IC at a time when the angle of the rotating gantry is 90°.

The calculation is implemented assuming that the phase at the inlet of the rotating gantry is −1.85 (=−(2.9+0.8)/2). The phase is the same as the phase after pivoting a half round; therefore, it can be considered that the phase at the inlet of the rotating gantry is 0.15±m/2 (=−1.85±n/2). The characters n and m are natural numbers. Accordingly, the foregoing equation can be modified to the equation below.

$$-(2.9+0.8)/2=-0.85=0.15-2/2$$

The above equation suggests that the same result is obtained by utilizing the average value of the decimal pare 0.9 of 2.9 and the decimal part 0.8 of 0.8.

Next, the half-integer part will be considered. The part, of 2.9, obtained by subtracting the half-integer part from 2.9 is 0.4. The part, of 0.8, obtained by subtracting the half-integer part from 0.8 is 0.3. As is the case with the foregoing equation, the equation below is established in this case and the same result is obtained.

$$-(0.4+0.3)/2=-0.35=0.15-\frac{1}{2}$$

When expressed by an angle, the phase is expressed by the angle obtained by pivoting (54°±180°) counterclockwise.

The x-direction spreads (projection length in FIGS. 38 through 40) at the isocenter IC at times when the gantry angle are 0° and 90° are approximately the same as each other. In the case where the gantry angle is between 0° and 90°, although it is not simple to specify the beam size because the x-direction and y-direction spreads are combined; however, the beam size can become constant without depending on the gantry angle, because the spreads are within the above ranges.

Figure 17A:
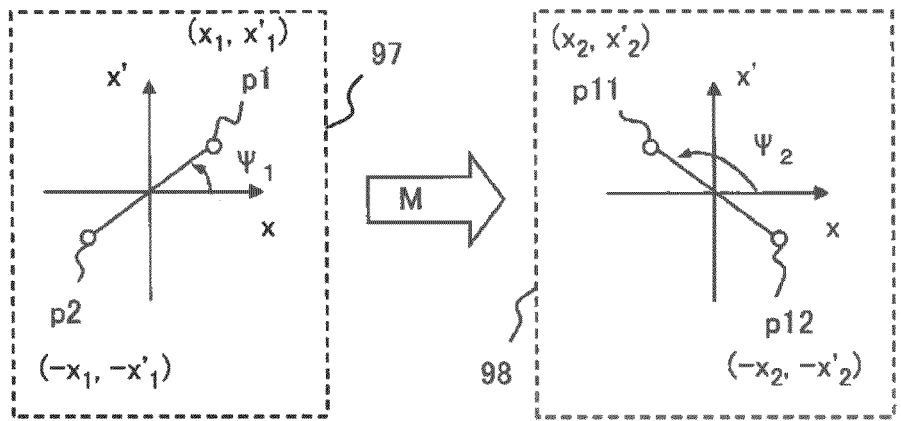
FIG. 17A and FIG. 17B are graphs representing the x-direction phase space distribution of a charged particle in a fixed transport unit of a charged particle beam transport system according to the present invention.
Figure 17B:
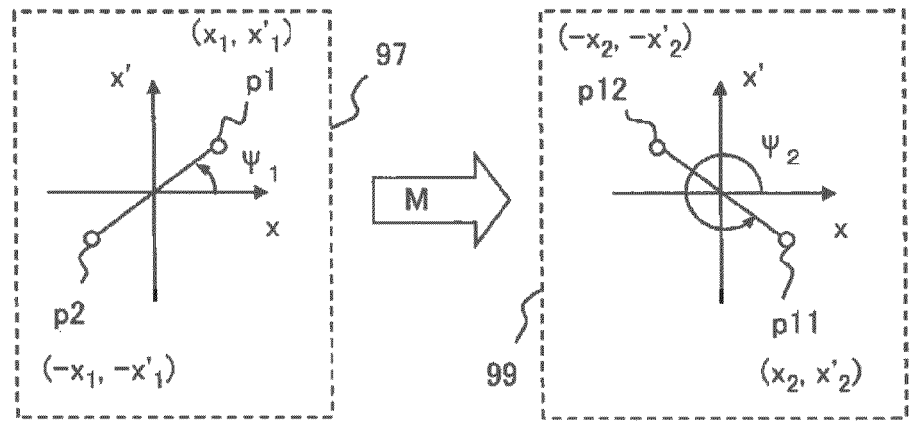

Because the condition 1 is as a matter of course, the conditions 2 and 3 will be specifically explained. FIG. 17A and FIG. 17B are graphs representing the x-direction phase space distribution of a charged particle in a charged particle beam transport system according to the present invention. FIG. 17A represents an example in which at the outlet of the fixed transport unit 61, the x-direction phase space distribution has become an x-direction phase distribution 98; FIG. 17B represents an example in which at the outlet of the fixed transport unit 61, the x-direction phase space distribution has become an x-direction phase distribution 99. An x-direction phase distribution 97 is a phase space distribution at the outlet of the accelerator 54. The x-direction phase space distributions 98 and 99 are phase space distributions at the outlet of the fixed transport unit 61, i.e., at the inlet of the rotating deflection unit 60. The x-direction phase distributions 97, 98, and 99 are represented as linear distributions. The coordinates of an end point p1 of the x-direction phase distribution 97 are $(x_1, x'_1)$; the coordinates of an end point p2 of the x-direction phase distribution 97 are $(-x_1, -x'_1)$. A phase $\Psi_1$ denotes a phase of the x-direction phase distribution 97; a phase $\Psi_2$ denotes a phase of the x-direction phase distribution 98 or 99.

Each of the x-direction phase distributions 98 and 99 suggests that the end point p1 at the inlet of the rotating deflection unit 60 has moved to an end point p11 $(x_2, x'_2)$ and the end point p2 at the inlet of the rotating deflection unit 60 has moved to an end point p12 $(-x_2, -x'_2)$. The difference between the x-direction phase distribution 98 and the x-direction phase distribution 99 is that the respective quadrants in which the end points p11 exist are opposite to each other.

The condition 2 signifies that at the inlet of the rotating deflection unit 60, $\beta_y$, $\alpha_y$, $\eta_x$, $\eta'_x$, $\eta_y$, and $\eta'_y$ satisfy the conventional conditions; that is to say, $\eta_x$, $\eta'_x$, $\eta_y$, and $\eta'_y$ are all "0" and $\beta_y$ and $\alpha_y$ have values that satisfy the beam condition at the isocenter IC. The condition 2 will be referred to as a constraint condition 1.

The condition 3 signifies that the transport matrix M is determined so that the x-direction phase distributions 98 and 99 having the end point p11 $(x_2, x'_2)$ and the end point p12 $(-x_2, -x'_2)$ are established at the outlet of the fixed transport unit 61 (at the inlet of the rotating deflection unit 60). The condition 3 will be referred to as a constraint condition 2. The transport matrix M is a function of Twiss parameters and phase advances at the inlet and outlet of the fixed transport unit 61 of the charged particle beam transport system 59; thus, when expressed by use of the Twiss parameters, the condition is given by the equation (5). When utilized as parameters, the betatron functions $\beta$ and $\alpha$ are referred to as Twiss parameters.

$$x_2 = A_1 x_1 + \sqrt{\beta_1 \beta_2} \sin(\Delta\psi) x'_1$$

$$x'_2 = B_1 x_1 + C_1 x'_1 \quad (5)$$

where $A_1$, $B_1$, and $C_1$ in the equation (5) are given by the equations (6).

$$A_1 = \sqrt{\frac{\beta_2}{\beta_1}} [\cos(\Delta\psi) + \alpha_1 \sin(\Delta\psi)] \quad (6)$$

$$B_1 = \frac{\{1 + \alpha_1 \alpha_2\} \sin(\Delta\psi) + \{\alpha_2 - \alpha_1\} \cos(\Delta\psi)}{\sqrt{\beta_1 \beta_2}}$$

$$C_1 = \sqrt{\frac{\beta_2}{\beta_1}} [\cos(\Delta\psi) - \alpha_2 \sin(\Delta\psi)]$$

The betatron functions $\beta_1$ and $\alpha_1$ are Twiss parameters at the inlet of the fixed transport unit 61; $\beta_2$ and $\alpha_2$ are Twiss parameters at the outlet of the fixed transport unit 61; $\Delta\Psi$ is a phase advance over a section from the inlet to the outlet of the fixed transport unit 61 and corresponds to $\Psi_2 - \Psi_1$. The coordinates $x_1$ and $x'_1$ are determined through designing of launch from the accelerator 54; $x_2$ and $x'_2$ are determined through designing of the rotating gantry (rotating deflection unit 60) at a time when the beam size is made to be independent of the angle.

In the charged particle beam transport system 59 according to Embodiment 1 of the present invention, the phase $\phi_{fx}$ of the x-direction phase space distribution at the inlet of the rotating deflection unit 60 is made to be a phase obtained by adding a minus (−) sign to the average value of the respective decimal parts of the phase advances over a section from the inlet to the outlet of the rotating deflection unit 60 at times when the gantry angles are $\theta_1$ and $\theta_2$ that are different by 90° from each other. In other words, the phase of the x-direction phase distribution phase 98 (or 99) having the end point p11 $(x_2, x'_2)$ and the end point p12 $(-x_2, -x'_2)$ is made to be the phase $\phi_{fx}$ obtained by adding a minus (−) sign to the average value of the respective decimal parts of the phase advances over a section from the inlet to the outlet of the rotating deflection unit 60 at times when the gantry angles are $\theta_1$ and $\theta_2$ that are different by 90° from each other. The phase $\Psi_2$ of the x-direction phase distribution 98 (or 99) is the phase $\phi_{fx}$.

The designing flow for the fixed transport unit 61 of the charged particle beam transport system 59 that satisfies the conditions 1 through 3 is as follows.

Step S1: as usual, the arrangement and polarities of the quadrupole electromagnets 49 are determined by use of Twiss parameters as conditions. In this case, when the arrangement of the quadrupole electromagnets 49 is added to the degree of flexibility, the steps thereafter become too long; therefore, the base of the quadrupole electromagnets 49 is created. As a result, the steps thereafter can be shortened.

Step S2: an arbitrary ellipse is drawn in such a way as to make contact with the x-direction phase space distribution at the outlet of the fixed transport unit 61 (at the inlet of the rotating deflection unit 60), and then Twiss parameters are calculated. The phase $\Psi_2$ of the ellipse is also calculated. Because the beam distribution at the outlet of the fixed transport unit 61 (at the inlet of the rotating deflection unit 60) is important, the outlet is utilized as the reference.

Step S3: the Twiss parameters at the inlet of the fixed transport unit 61 are calculated by use of the equation (5). In this situation, as $\Delta\Psi$, an arbitrary value is assumed, and the phase $\Psi_1$ at the inlet is calculated from $\Psi_2$ and $\Delta\Psi$. In order to confirm from the Twiss parameters that the charged particle beam 31 can pass through the fixed transport unit 61, Steps S2 and S3 are repeated so that the ellipse (of course, the emittances are the values thereof at the outlet) corresponding to the Twiss parameters at the inlet contains the beam distribution at the inlet. In the case where the beam size is confirmed by performing tracking every time, the confirmation method is not limited thereto.

Step S4: the fixed transport unit 61 is designed in such a way that the Twiss parameters at the inlet and outlet of the fixed transport unit 61 and the constraint condition 2 are satisfied. The conventional designing method corresponds to implementation of Step S4.

Step S5: Steps S2 through S4 are repeated until an appropriate solution is found in Step S4. In the case where no solution is found, Step S1 is resumed and the arrangement and polarities of the quadrupole electromagnets 49 are changed.

It is confirmed whether or not the result of the foregoing designing satisfies the conventional designing conditions. This confirmation makes it possible to smoothly implement adjustment work after installation of the charged particle beam transport system 59. Moreover, even in the case where the arrangement and polarities, of the quadrupole electromagnets 49, that have been determined in Step S1 are adhered to, it is made possible to smoothly implement adjustment work after installation of the charged particle beam transport system 59.

In the rotating deflection unit 60 of the charged particle beam transport system 59 according to Embodiment 1, a new inlet condition in which the phase $\phi_{ix}$ of the x-direction phase space distribution at the inlet is added to the inlet condition in the conventional designing is utilized, so that without changing the strengths of the three deflection electromagnets 10a, 10b, and 10c and the four quadrupole electromagnets 11a, 11b, 11c, and 11d, a beam size having a low rotation dependency can be realized at the isocenter IC even when asymmetry in the emittances exists at the inlet of the rotating deflection unit 60 of the charged particle beam transport system 59.

As described above, in the charged particle beam transport system 59 according to Embodiment 1, letting x-direction denote a direction on a circular orbit plane of the accelerator in a plane perpendicular to the traveling direction of the charged particle beam 31 at a launching position of the accelerator 54 and y-direction denote a direction perpendicular to x-direction in a plane perpendicular to the traveling direction of the charged particle beam 31, the charged particle beam 31 launched from the accelerator 54 becomes a charged particle beam whose x-direction and y-direction emittances are different from each other; the charged particle beam transport system 59, which transports the charged particle beam 31 to the particle beam irradiation apparatus 58 mounted in a rotating gantry that can rotate around the isocenter IC, includes the rotating deflection unit 60 that is mounted in the rotating gantry and rotates around the gantry rotation axle 15 of the rotating gantry and the fixed transport unit 61 that ranges from the accelerator 54 to the rotating deflection unit 60; the rotating deflection unit 60 includes two or more deflection electromagnets 10. The charged particle beam transport system 59 according to Embodiment 1 is characterized in that when viewed from the gantry rotation axle, a gantry angle is defined as an angle between the beam center line 14 of the particle beam irradiation apparatus 58 and y-direction axis of the charged particle beam 31 at an inlet of the rotating deflection unit 60, in that a gantry reference angle is defined as an angle of the rotating gantry at which the charged particle beam 31 is transported in such a way that x-direction and y-direction emittances at the launching position of the accelerator 54 are separated and the respective emittances are maintained, in that a first phase advance is defined as a change in a phase, of a phase space distribution of the charged particle beam 31, that changes when the charged particle beam 31 travels from the inlet of the rotating deflection unit 60 to the isocenter IC in the case where the gantry angle is the gantry reference angle, in that a second phase advance is defined as a change in a phase, of the phase space distribution of the charged particle beam 31, that changes when the charged particle beam 31 travels from the inlet of the rotating deflection unit 60 to the isocenter IC in the case where the gantry angle is pivoted by 90° from the gantry reference angle, and in that in the fixed transport unit 61, a phase of the phase space distribution of the charged particle beam 31 at the inlet of the rotating deflection unit 60 coincides with a phase determined by a calculation based on an average value of the first phase advance and the second phase advance; therefore, in the fixed transport unit 61, the phase $\phi_{ix}$ of the x-direction phase space distribution at the inlet of the rotating deflection unit 60 can be made to be a predetermined phase, i.e., the phase space distribution of the charged particle beam 31 at the inlet of the rotating deflection unit 60 can be made to be a predetermined phase space distribution whose phase is, for example, a phase determined by a calculation based on the average value of the first phase advance and the second phase advance; thus, even for a beam having an extremely small x-direction emittance, at the inlet of the rotating deflection unit 60 of the charged particle beam transport system 59, that is a characteristic of a slow-extraction method, a beam size having a low rotation dependency can be realized at the isocenter IC.

As described above, in the particle beam therapy system 51 according to Embodiment 1, letting x-direction denote a direction on a circular orbit plane of the accelerator 54 in a plane perpendicular to a traveling direction of the charged particle beam 31 at a launching position of the accelerator 54 and y-direction denote a direction perpendicular to x-direction in a plane perpendicular to the traveling direction of the charged particle beam 31, the charged particle beam 31 accelerated by the accelerator 54 becomes a charged particle beam whose x-direction and y-direction emittances are different from each other; the particle beam therapy system 51 includes the beam generation apparatus 52 that generates the charged particle beam 31 and accelerates it by means of the accelerator 54, the charged particle beam transport system 59 that transports the charged particle beam 31, the particle beam irradiation apparatus 58 that irradiates the charged particle beam 31 transported by the charged particle beam transport system 59 onto the irradiation subject 45, and a rotating gantry that is equipped with the particle beam irradiation apparatus and can rotate around an isocenter; the charged particle beam transport system 59 is provided with the rotating deflection unit 60 that is mounted in the rotating gantry and rotates around the gantry rotation axle 15 of the rotating gantry and the fixed transport unit 61 that ranges from the accelerator 54 to the rotating deflection unit 60; the rotating deflection unit 60 includes two or more deflection electromagnets 10; the charged particle beam transport system 59 is characterized in that when viewed from the gantry rotation axle, a gantry angle is defined as an angle between the beam center line 14 of the particle beam irradiation apparatus 58 and y-direction axis of the charged particle beam 31 at an inlet of the rotating deflection unit 60, in that a gantry reference angle is defined as an angle of the rotating gantry at which the charged particle beam 31 is transported in such a way that x-direction and y-direction emittances at the launching position of the accelerator 54 are separated and the respective emittances are maintained, in that a first phase advance is defined as a change in a phase, of a phase space distribution of the charged particle beam 31, that changes when the charged particle beam 31 travels from the inlet of the rotating deflection unit 60 to the isocenter IC in the case where the gantry angle is the gantry reference angle, in that a second phase advance is defined as a change in a phase, of the phase space distribution of the charged particle beam 31, that changes when the charged particle beam 31 travels from the inlet of the rotating deflection unit 60 to the isocenter IC in the case where the gantry angle is pivoted by 90° from the gantry reference angle, and in that in the fixed transport unit 61, a phase of the phase space distribution of the charged particle beam 31 at the inlet of the rotating deflection unit 60 coincides with a phase determined by a calculation based on an average value of the first phase advance and the second phase advance; therefore, in the fixed transport unit 61, the phase $\phi_{ix}$ of the x-direction phase space distribution at the inlet of the rotating deflection unit 60 can be made to be a predetermined phase, i.e., the phase space distribution of the charged particle beam 31 at the inlet of the rotating deflection unit 60 can be made to be a predetermined phase space distribution whose phase is, for example, a phase determined by a calculation based on the average value of the first phase advance and the second phase advance; thus, even for a beam having an extremely small x-direction emittance, at the inlet of the rotating deflection unit 60 of the charged particle beam transport system 59, that is a characteristic of a slow-extraction method, a beam size having a low rotation dependency can be realized at the isocenter IC.

Embodiment 2

A charged particle beam transport system 59 according to Embodiment 2 of the present invention will be explained. In Embodiment 2, the x-direction phase space distribution is approximated with a linear distribution having end points, and a fixed transport unit 61 of a charged particle beam transport system 59 is configured in such a way that a linear distribution having end points calculated by use of a matrix that is partially extracted from the transport matrix in the equation (3) is realized at the inlet of a rotating deflection unit 60 of the charged particle beam transport system 59. As described above, the x-direction phase space distribution of a charged particle beam 31 at the inlet of the rotating deflection unit 60 is controlled, so that the charged particle beam transport system 59 absorbs the difference in emittances, caused when a beam is launched from an accelerator 54 in a slow-extraction manner, and that a beam size having a small rotation dependency can be realized at an isocenter IC.

Beam designing for the rotating deflection unit 60 of the charged particle beam transport system 59 according to Embodiment 2 of the present invention will be explained. As explained in Embodiment 1, assuming that as is the case with the conventional method, a beam characterized by the conditions "$\eta_x=0, \eta'_x=0, \eta_y=0,$ and $\eta'_y=0$" appears at the inlet of the rotating deflection unit 60, the momentum dispersion function $\eta$ is designed in such a way that at the outlet of the rotating deflection unit 60, the conditions "$\eta_x=0, \eta'_x=0, \eta_y=0,$ and $\eta'_y=0$" are satisfied. Moreover, attention will be paid to the case where the gantry angle is 0° (or 180°) and the case where the gantry angle is 90° (or 270°). In the case where the deflection electromagnets of the rotating deflection unit 60 include only deflection electromagnets that perform deflection on the planes parallel to and perpendicular to the deflection electromagnet of the fixed transport unit 61, a transport matrix given by the equation (3) in which no coupling between the x direction and the y direction exists is obtained, as it the case with Embodiment 1.

Unlike Embodiment 1, the restriction ($\alpha_x=\alpha_y$) is not provided in the conditions at the inlet and the outlet of the rotating deflection unit 60. That is to say, in the beam designing for the rotating deflection unit 60 according to Embodiment 2, the conditions at the inlet and outlet of the rotating deflection unit 60 are established as follows:

The conditions at the inlet of the rotating deflection unit 60 are $\beta_x=\beta_y$, $\eta_x=0, \eta'_x=0, \eta_y=0,$ and $\eta'_y=0$.

The conditions at the outlet of the rotating deflection unit 60 are $\eta_x=0, \eta'_x=0, \eta_y=0,$ and $\eta'_y=0$.

By establishing the conditions at the inlet and outlet of the rotating deflection unit 60 in such a way as described above, i.e., by simplifying the conditions as much as possible, the beam designing for the rotating deflection unit 60 can be implemented with a few number of adjustment parameters.

The adjustment parameters in the equation (3) are $m_{11}$, $m_{12}$, $m_{21}$, $m_{22}$, $m_{33}$, $m_{34}$, $m_{43}$, and $m_{44}$.

Figure 18A:
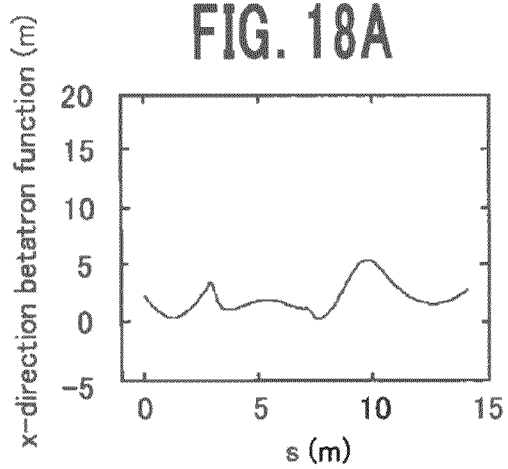
FIG. 18A and FIG. 18B are graphs representing the betatron function of a charged particle over a section from the rotating deflection unit to an isocenter according to Embodiment 2 of the present invention.
Figure 18B:
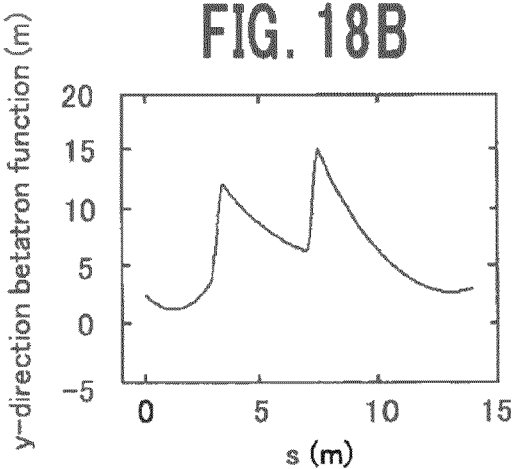
Figure 19A:
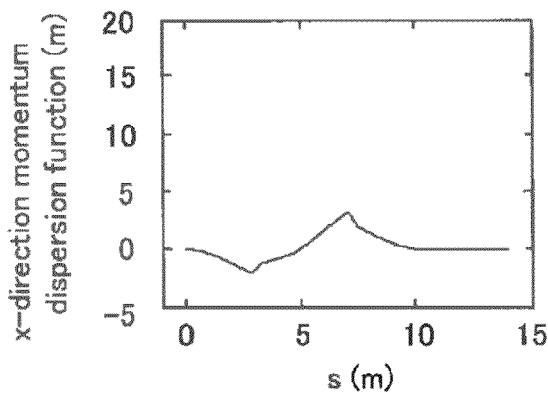
FIG. 19A and FIG. 19B are graphs representing the momentum dispersion function of a charged particle over a section from the rotating deflection unit to an isocenter according to Embodiment 2 of the present invention.
Figure 19B:
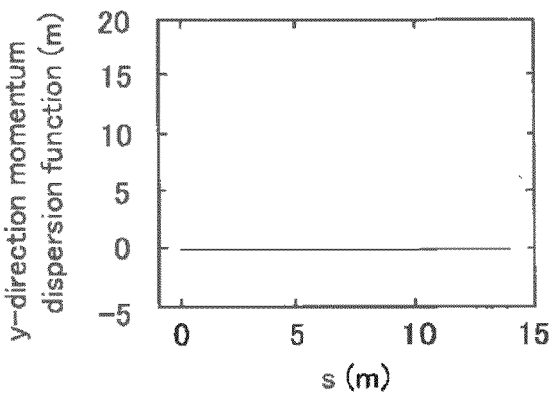

FIGS. 18A, 18B and 19A, 19B represent the betatron function $\beta$ and the momentum dispersion function $\eta$, respectively, of the rotating deflection unit 60 (refer to FIG. 3) according to Embodiment 2 of the present invention. FIG. 18A and FIG. 18B are graphs representing the betatron function of a charged particle over a section from the rotating deflection unit to the isocenter IC according to Embodiment 2 of the present invention. The abscissa denotes the s-direction distance; the ordinate denotes the betatron function $\beta$. In FIG. 18A and FIG. 18B, the betatron function $\alpha$ is not represented. FIG. 18A represents the x-direction betatron function $\beta$; FIG. 18B represents the y-direction betatron function $\beta$. FIG. 19A and FIG. 19B are graphs representing the momentum dispersion function of a charged particle over a section from the rotating deflection unit to the isocenter IC according to Embodiment 2 of the present invention. The abscissa denotes the s-direction distance; the ordinate denotes the momentum dispersion function $\eta$. FIG. 19A represents the x-direction momentum dispersion function $\eta$; FIG. 19B represents the y-direction momentum dispersion function $\eta$. In each of FIGS. 18A, 18B, 19A, and 19B, the inlet of the rotating deflection unit 60 is at s=0 m, and the outlet of the rotation deflection unit 60 is approximately at s=14 m, i.e., the right end. In Embodiment 2, the four quadrupole electromagnets 11a, 11b, 11c, and 11d realizes a transport matrix in which the beam characteristics at the isocenter IC become excellent.

There will be considered an example in which in the case where the electromagnet arrangement in the rotation deflection unit 60 according to Embodiment 2 of the present invention is the electromagnet arrangement of the rotation deflection unit 60 illustrated in FIG. 3 and the respective electromagnets have strengths in such a way that the betatron function and the momentum dispersion function represented in FIGS. 18A, 18B and 19A, 19B, respectively, are established, the beam designing for the rotation deflection unit 60 is implemented by use of the transport matrix of the rotation deflection unit 60. Part of the transport matrix, in this case, of the rotation gantry is selected and extracted. The matrix obtained by extracting part of the transport matrix in equation (3) is given by the equation (7). A matrix obtained by extracting part of a transport matrix will be referred to as a selected matrix.

$$\begin{bmatrix} m_{11} & m_{12} \\ m_{33} & m_{34} \end{bmatrix} \quad (7)$$

The elements m11, m12, m33, and m34 in the matrix of the equation (7) are quantities for correlating the x-direction beam size and the y-direction beam size at the isocenter IC with the phase space distributions at the inlet of the rotating gantry, i.e., at the inlet of the rotating deflection unit 60. Based on these quantities, an ideal x-direction phase space linear distribution at the inlet of the rotating gantry is determined as follows.

The quantity that characterizes the phase space linear distribution is the coordinates (x, x') of an end point in the phase space. Accordingly, assuming that the coordinates (x, x') of the end point are unknown quantities, simultaneous equations of the equation (8) are derived by use of the transport matrix in the equation (7).

$$\begin{bmatrix} m_{11} & m_{12} \\ m_{33} & m_{34} \end{bmatrix} \begin{bmatrix} x \\ x' \end{bmatrix} = \begin{bmatrix} \sqrt{\beta_y \varepsilon_y} \\ \sqrt{\beta_y \varepsilon_y} \end{bmatrix} \quad (8)$$

The meaning of the equation (8) will be explained. The equation (8) is to make the beam size at a time when the gantry angle is 0° or 180° and the beam size at a time when the gantry angle is 90° or 270° coincide with each other. When there is realized an optical system (the charged particle beam transport system 59) that can make the respective beam sizes at times when the gantry angles are the foregoing two angles approximately coincide with each other, only neglectable difference is caused between the two angles.

When at the gantry inlet (at the inlet of the rotating deflection unit 60), there is realized a linear phase-space distribution, one end of which is the end-point coordinates (x, x') obtained by solving the equation (8) and the other end of which is the coordinates that is point-symmetry with the end-point coordinates (x, x') with respect to the origin, i.e., the coordinates (−x, −x'), a beam passes through the rotating deflection unit 60 designed according to the conventional setting method; thus, the rotation dependency of a beam size is eliminated at the isocenter IC.

Figure 20A:
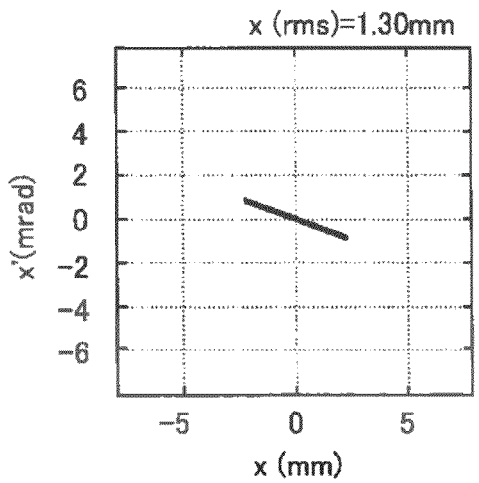
FIG. 20A and FIG. 20B are graphs representing the phase space distribution of a charged particle at the inlet of the rotating deflection unit according to Embodiment 2 of the present invention.
Figure 20B:
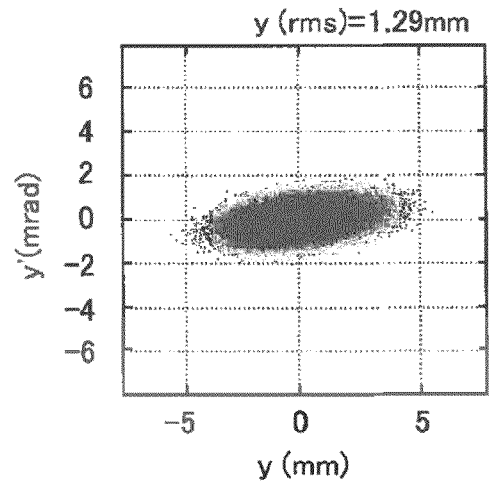

FIGS. 20A, 20B represent the phase space distribution, obtained through the foregoing procedure, of a charged particle at the inlet of the rotating deflection unit 60 according to Embodiment 2. Each of FIGS. 21A, 21B through 28A, 28B represents the phase space distribution of a charged particle at the isocenter IC of the rotating deflection unit 60 according to Embodiment 2.

FIGS. 21A, 21B through 28A, 28B are graphs representing the phase space distributions of a charged particle at the isocenter IC at times when the angles of the rotation deflection unit according to Embodiment 2 of the present invention are 0°, 30°, 60°, 90°, 120°, 150°, 180°, and 210°, respectively. The graph in each of FIGS. 21A through 28A represents the x-direction phase space distribution; the graph in each of FIGS. 21B through 28B represents the y-direction phase space distribution. In the graph in each of FIGS. 21A through 28A, the abscissa denotes the x-direction distance x, and the ordinate denotes the x-direction gradient x'. In the graph in each of FIGS. 21B through 28B, the abscissa denotes the y-direction distance y, and the ordinate denotes the y-direction gradient y'. The beam size (rms) represented in each graph is the beam size 1σ explained in Embodiment 1.

Figure 21A:
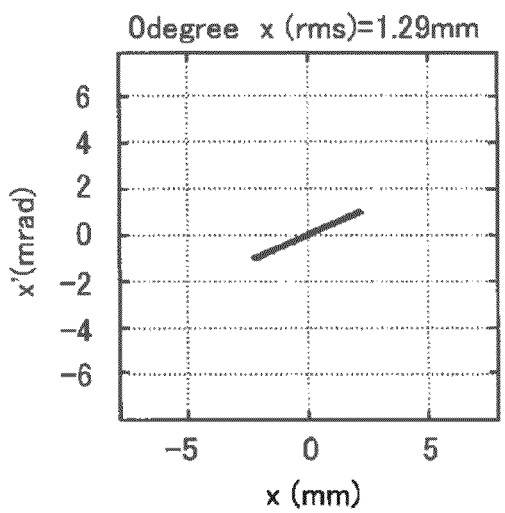
FIG. 21A and FIG. 21B are graphs representing the phase space distribution of a charged particle at an isocenter when the angle of the rotating deflection unit according to Embodiment 2 of the present invention is 0°.
Figure 21B:
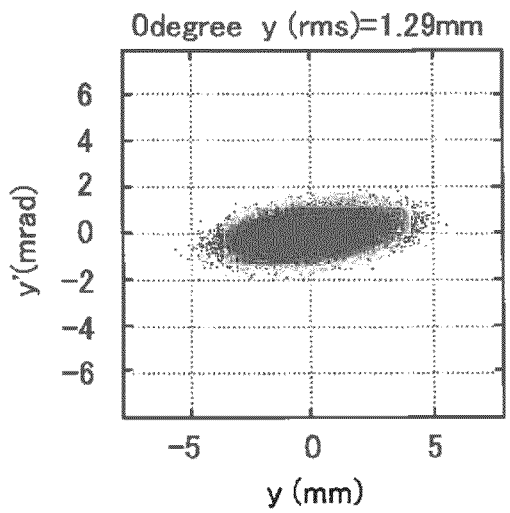
Figure 22A:
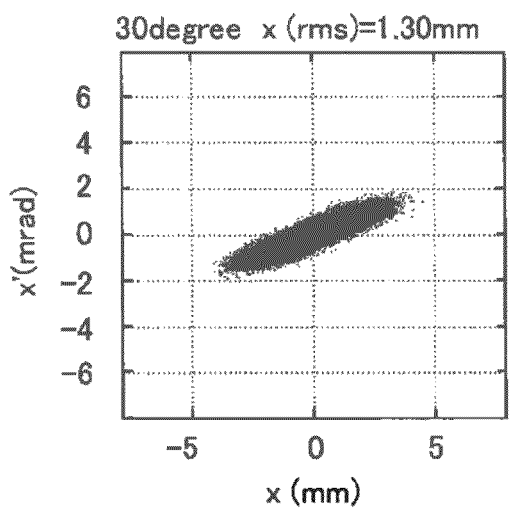
FIG. 22A and FIG. 22B are graphs representing the phase space distribution of a charged particle at an isocenter when the angle of the rotating deflection unit according to Embodiment 2 of the present invention is 30°.
Figure 22B:
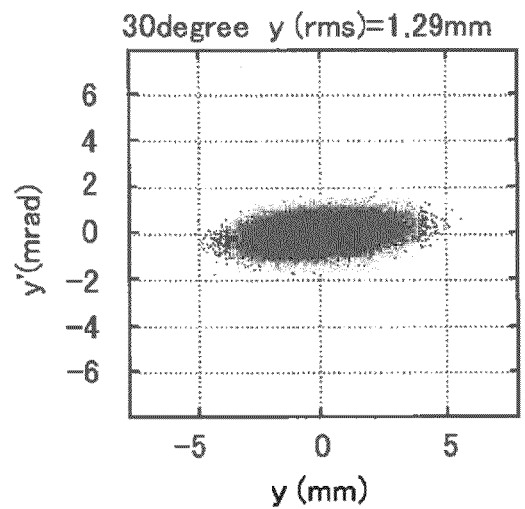
Figure 23A:
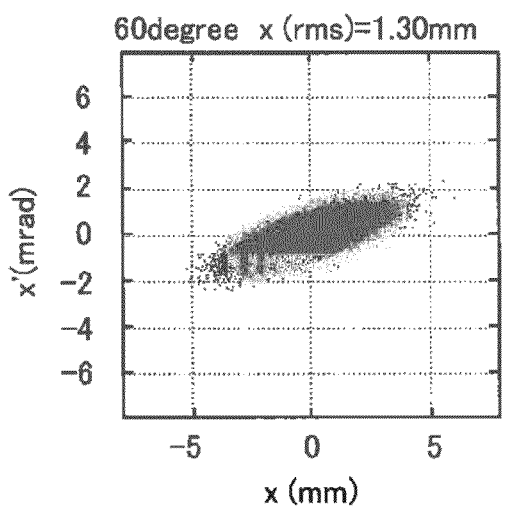
FIG. 23A and FIG. 23B are graphs representing the phase space distribution of a charged particle at an isocenter when the angle of the rotating deflection unit according to Embodiment 2 of the present invention is 60°.
Figure 23B:
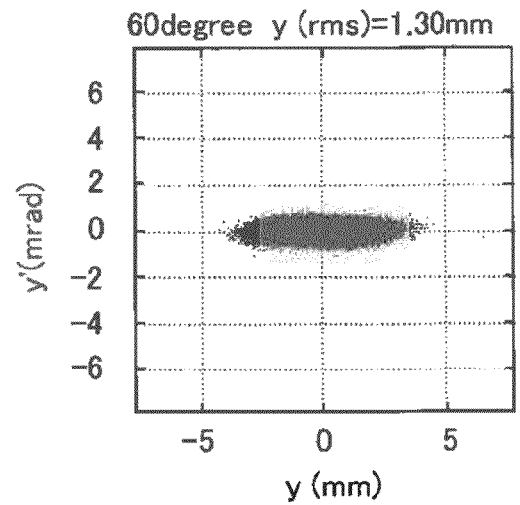
Figure 24A:
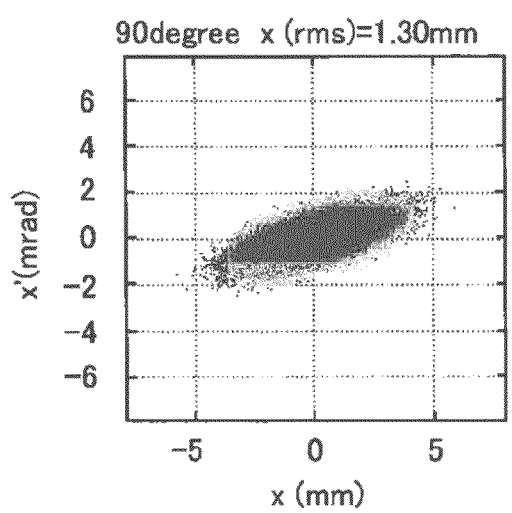
FIG. 24A and FIG. 24B are graphs representing the phase space distribution of a charged particle at an isocenter when the angle of the rotating deflection unit according to Embodiment 2 of the present invention is 90°.
Figure 24B:
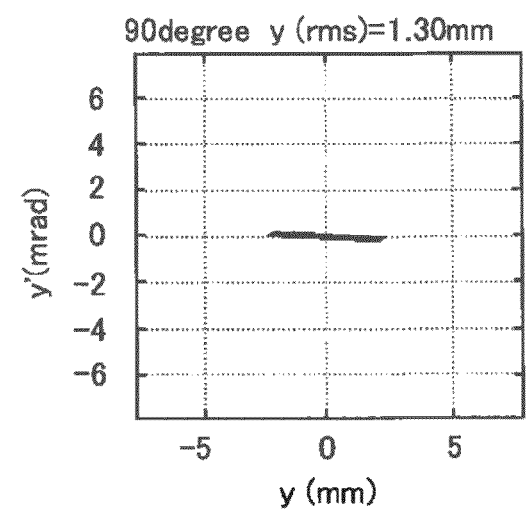

As represented in FIGS. 21A, 21B, in the case where the angle of the rotating deflection unit 60 is 0°, the x-direction beam size 1σ and the y-direction beam size 1σ are 1.29 mm and 1.29 mm, respectively. As represented in FIGS. 22A, 22B, in the case where the angle of the rotating deflection unit is 30°, the x-direction beam size 1σ and the y-direction beam size 1σ are 1.30 mm and 1.29 mm, respectively. As represented in FIGS. 23A, 23B, in the case where the angle of the rotating deflection unit is 60°, the x-direction beam size 1σ and the y-direction beam size 1σ are 1.30 mm and 1.30 mm, respectively. As represented in FIGS. 24A, 24B, in the case where the angle of the rotating deflection unit is 90°, the x-direction beam size 1σ and the y-direction beam size 1σ are 1.30 mm and 1.30 mm, respectively.

Figure 25A:
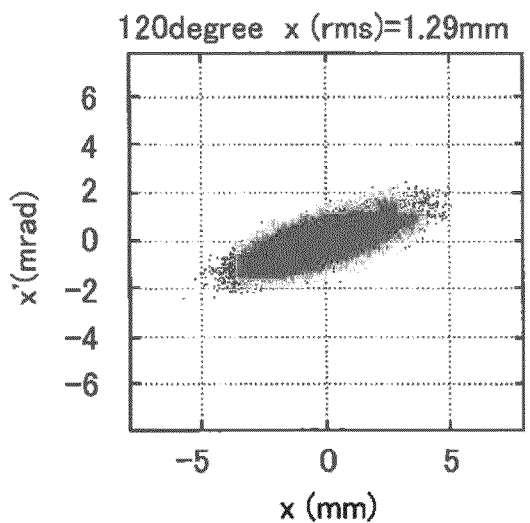
FIG. 25A and FIG. 25B are graphs representing the phase space distribution of a charged particle at an isocenter when the angle of the rotating deflection unit according to Embodiment 2 of the present invention is 120°.
Figure 25B:
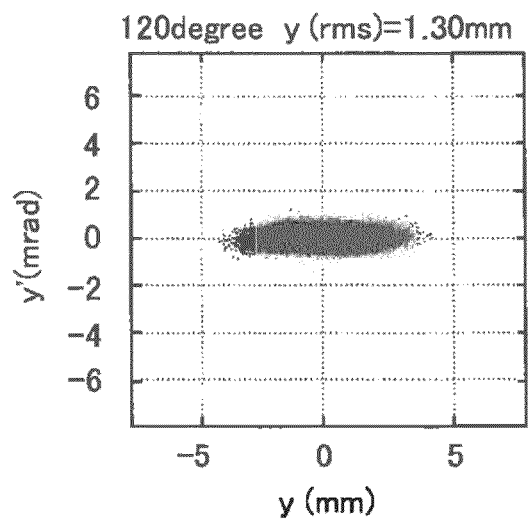
Figure 26A:
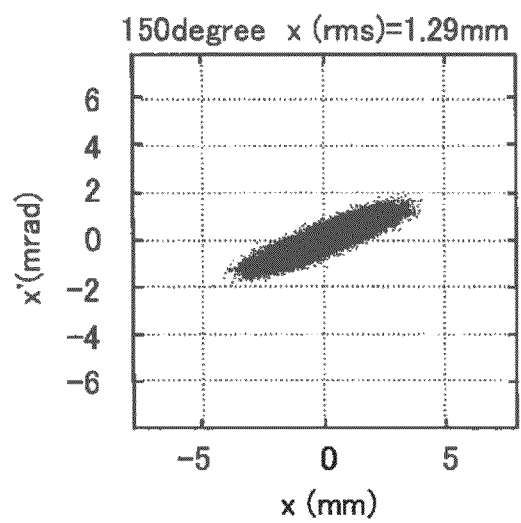
FIG. 26A and FIG. 26B are graphs representing the phase space distribution of a charged particle at an isocenter when the angle of the rotating deflection unit according to Embodiment 2 of the present invention is 150°.
Figure 26B:
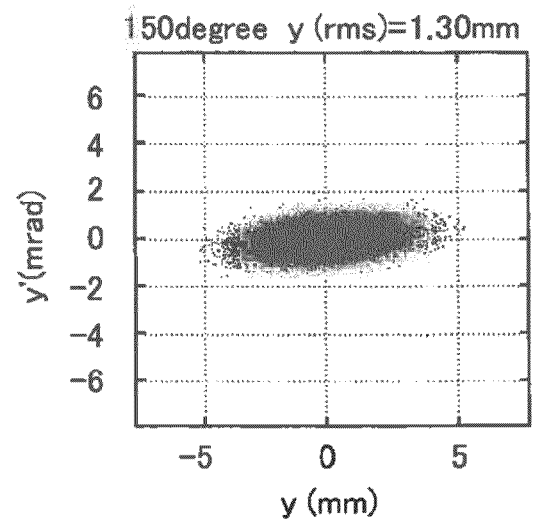
Figure 27A:
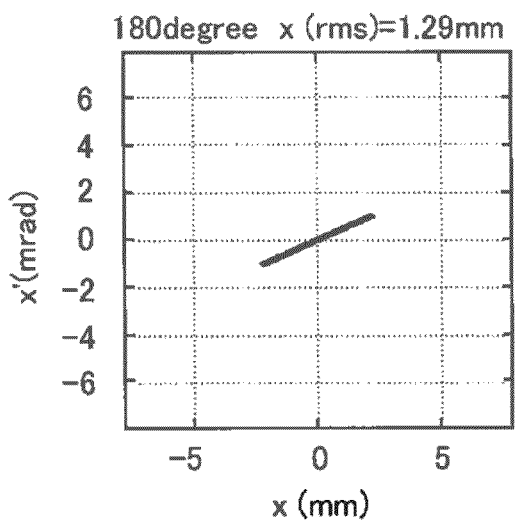
FIG. 27A and FIG. 27B are graphs representing the phase space distribution of a charged particle at an isocenter when the angle of the rotating deflection unit according to Embodiment 2 of the present invention is 180°.
Figure 27B:
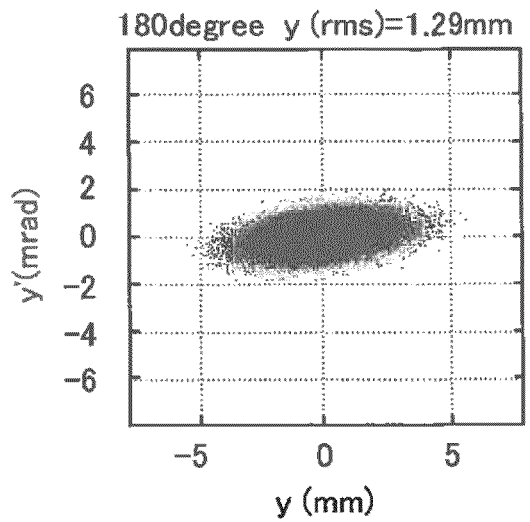
Figure 28A:
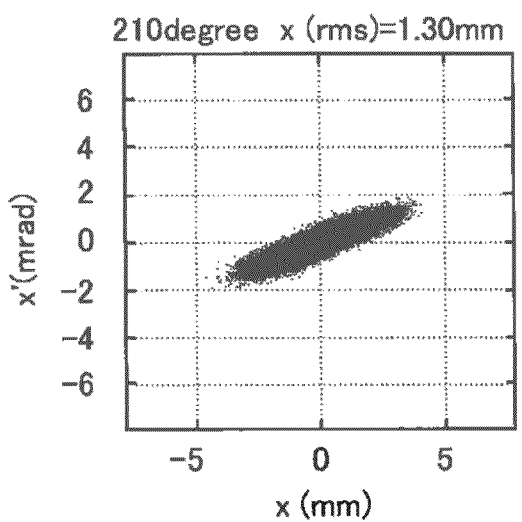
FIG. 28A and FIG. 28B are graphs representing the phase space distribution of a charged particle at an isocenter when the angle of the rotating deflection unit according to Embodiment 2 of the present invention is 210°.
Figure 28B:
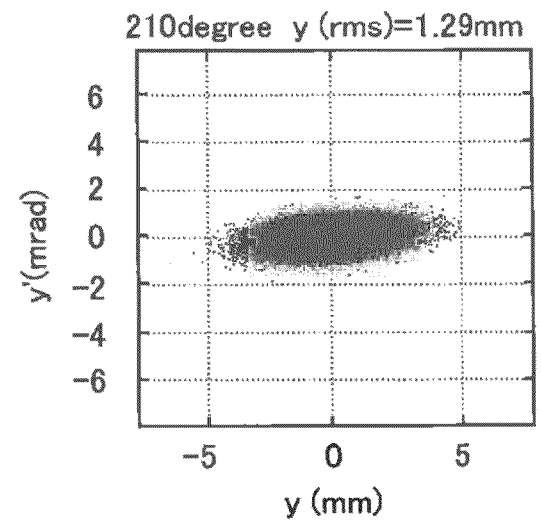

As represented in FIGS. 25A, 25B, in the case where the angle of the rotating deflection unit is 120°, the x-direction beam size 1θ and the y-direction beam size 1σ are 1.29 mm and 1.30 mm, respectively. As represented in FIGS. 26A, 26B, in the case where the angle of the rotating deflection unit is 150°, the x-direction beam size 1σ and the y-direction beam size 1σ are 1.29 mm and 1.30 mm, respectively. As represented in FIGS. 27A, 27B, in the case where the angle of the rotating deflection unit is 180°, the x-direction beam size 1σ and the y-direction beam size 1σ are 1.29 mm and 1.29 mm, respectively. As represented in FIGS. 28A, 28B, in the case where the angle of the rotating deflection unit is 210°, the x-direction beam size 1σ and the y-direction beam size 1σ are 1.30 mm and 1.29 mm, respectively.

Figure 29:
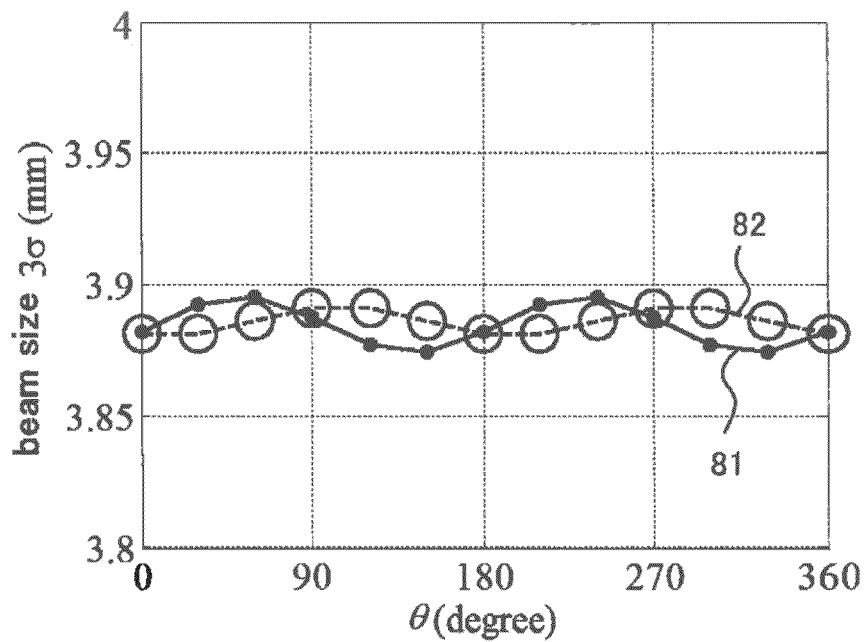
FIG. 29 is a graph representing the relationship between the beam size at an isocenter and the angle of the rotating deflection unit according to Embodiment 2 of the present invention.
Figure 30:
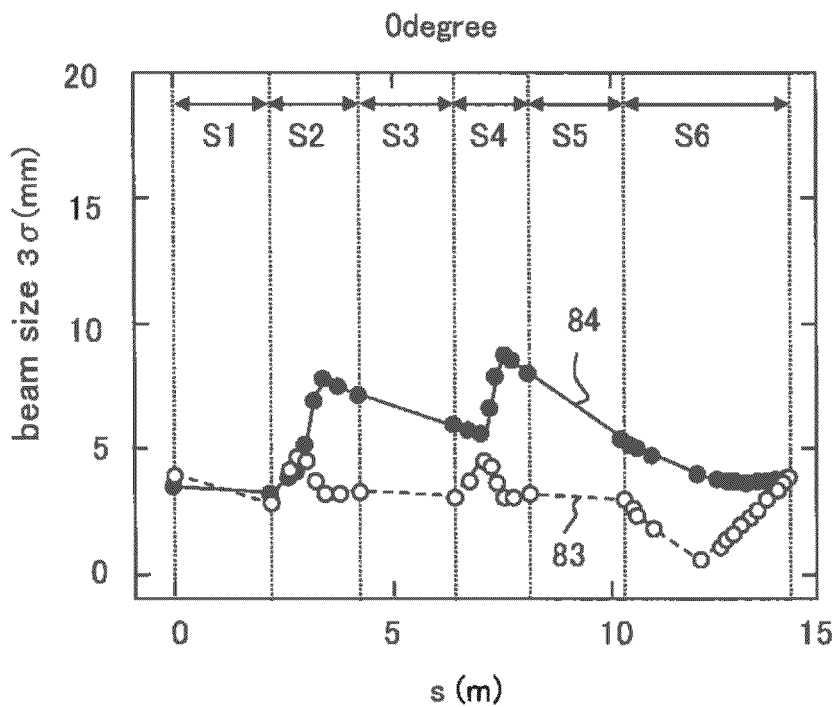
FIG. 30 is a graph representing the beam size when the angle of the rotating deflection unit according to Embodiment 2 of the present invention is 0°.

As represented in each of FIGS. 21A, 21B through 28A, 28B, although the shapes and phases of the x-direction and y-direction phase space distributions are different from each other, the x-direction beam size 1σ and the y-direction beam size 1σ are approximately the same as each other. FIG. 29 is a graph representing the relationship between the beam size at the isocenter IC and the angle of the rotating deflection unit according to Embodiment 2 of the present invention. The abscissa denotes the gantry angle θ of the rotating deflection unit 60, and the ordinate denotes the beam size 3σ that is thrice as large as the standard deviation σ. The characteristic 81 represented by a solid line is the x-direction characteristic, and the characteristic 82 represented by a broken line is the y-direction characteristic. When the rotating deflection unit 60 according to Embodiment 2 is configured in such a way as described above, there can be realized an approximately constant beam size that does not depend on the rotation angle of the rotating deflection unit 60, i.e., the rotation angle of the rotating gantry.

With regard to the fixed transport unit 61 of the charged particle beam transport system 59 according to Embodiment 2, the outlet of the fixed transport unit 61 is realized by use of a linear phase-space distribution, one end of which is the end-point coordinates (x, x') obtained by solving the equation (8) and the other end of which is the coordinates that is point-symmetry with the end-point coordinates (x, x') with respect to the origin, i.e., the coordinates (−x, −x'), in addition to the conditions at the inlet of the rotating deflection unit 60, i.e., $\beta_x = \beta_y$, $\eta_x = 0$, $\eta'_x = 0$, $\eta_y = 0$, and $\eta_y = 0$.

The designing flow for the fixed transport unit 61 is the same as the designing flow explained in Embodiment 1. However, unlike Embodiment 1, the limiting conditions "$\beta_x = \beta_y$, and $\alpha_x = \alpha_y$" in the constraint conditions are not set in Embodiment 2.

FIGS. 30 and 33 through 37 are graphs representing the beam sizes of a charged particle over a section from the inlet of the rotating deflection unit to the isocenter at times when the angles of the rotation deflection unit according to Embodiment 2 of the present invention are 0°, 30°, 60°, 90°, 120°, and 150°, respectively. The abscissa denotes the s-direction distance; the ordinate denotes the beam size 3σ. In each of FIGS. 30 and 33 through 37, the sections S1, S3, and S5 are sections where a particle bean passes through the deflection electromagnets 10a, 10b, and 10c, respectively; the section S2 is a section where the quadrupole electromagnets 11a and 11b are arranged; the section S4 is a section where the quadrupole electromagnets 11c and 11d are arranged. The section S6 is a section ranging from the outlet of the deflection electromagnet 10c, i.e., the outlet of the rotating deflection unit 60 to the isocenter IC.

Figure 31:
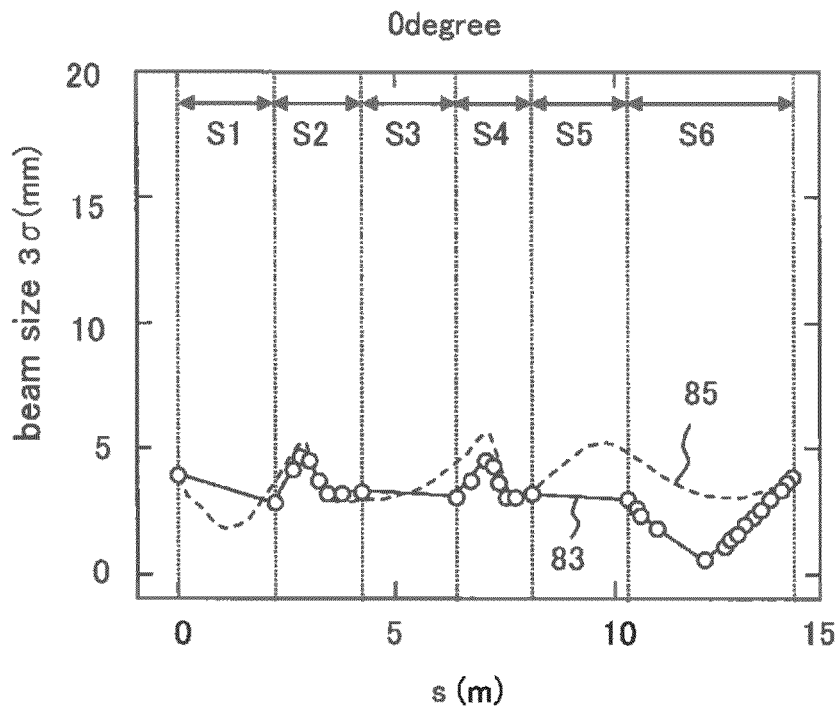
FIG. 31 is a graph representing the x-direction beam size when the angle of the rotating deflection unit according to Embodiment 2 of the present invention is 0°.
Figure 32:
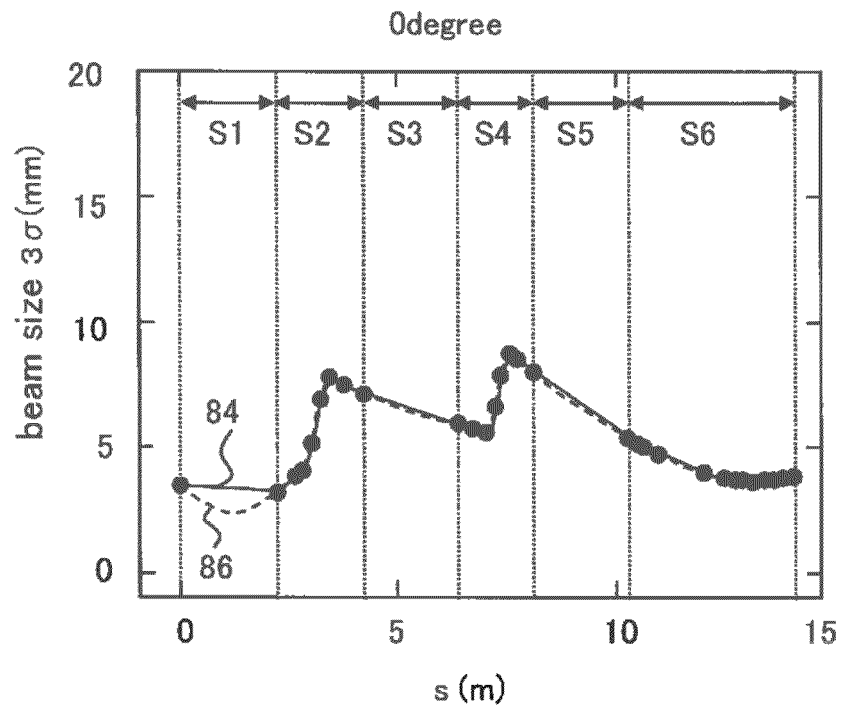
FIG. 32 is a graph representing the y-direction beam size when the angle of the rotating deflection unit according to Embodiment 2 of the present invention is 0°.
Figure 33:
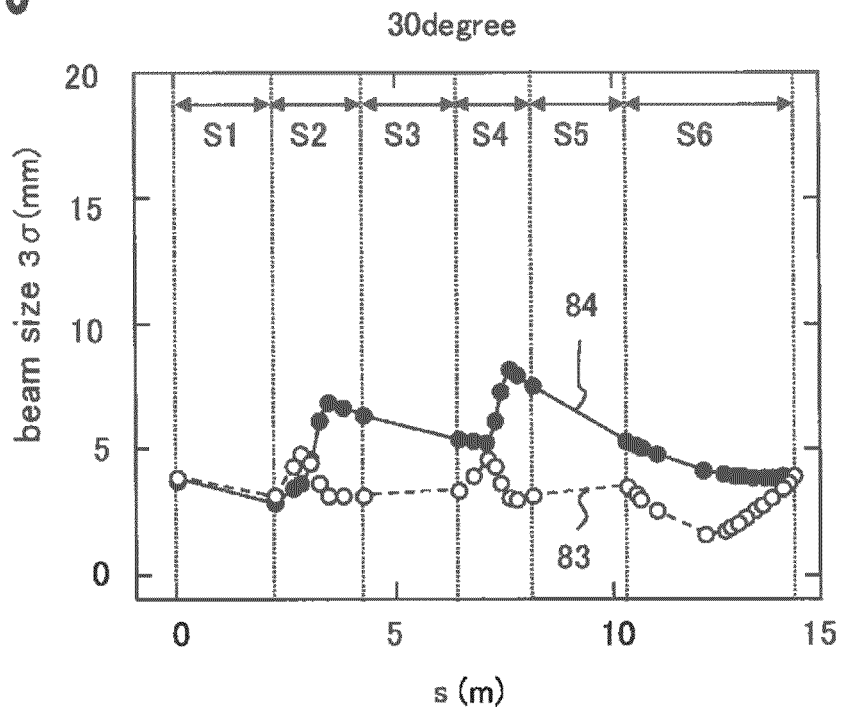
FIG. 33 is a graph representing the beam size when the angle of the rotating deflection unit according to Embodiment 2 of the present invention is 30°.
Figure 34:
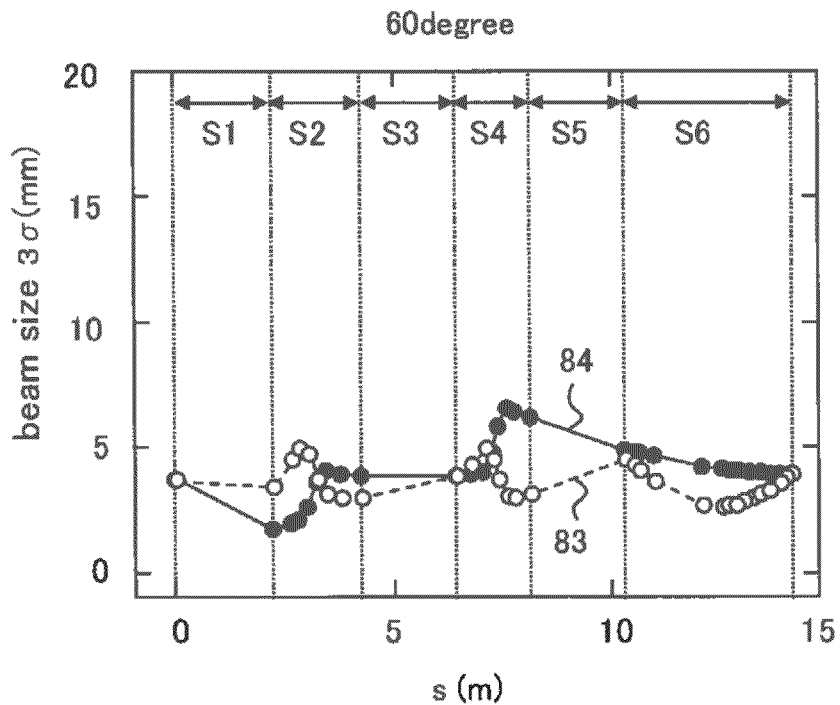
FIG. 34 is a graph representing the beam size when the angle of the rotating deflection unit according to Embodiment 2 of the present invention is 60°.
Figure 35:
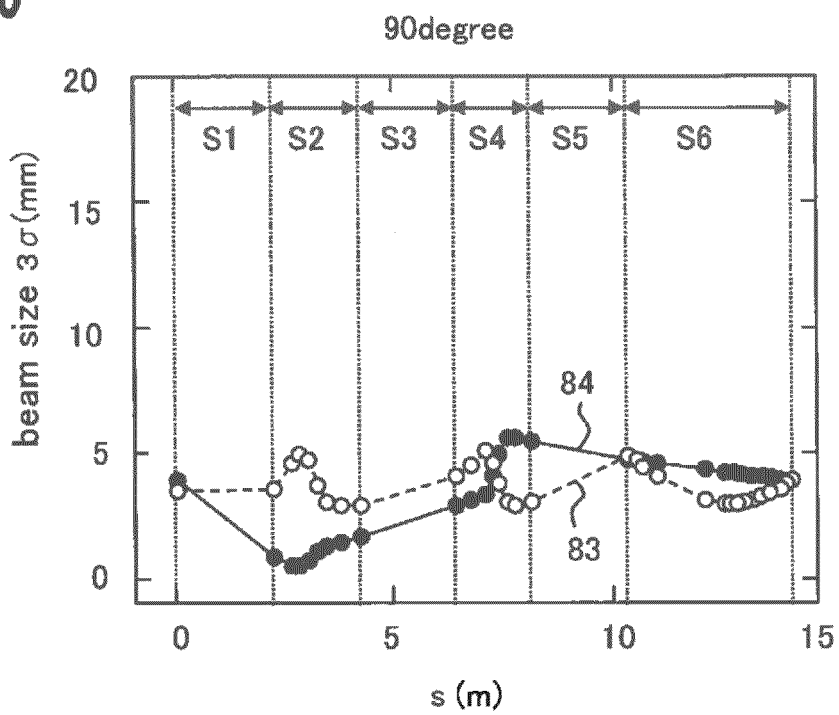
FIG. 35 is a graph representing the beam size when the angle of the rotating deflection unit according to Embodiment 2 of the present invention is 90°.
Figure 36:
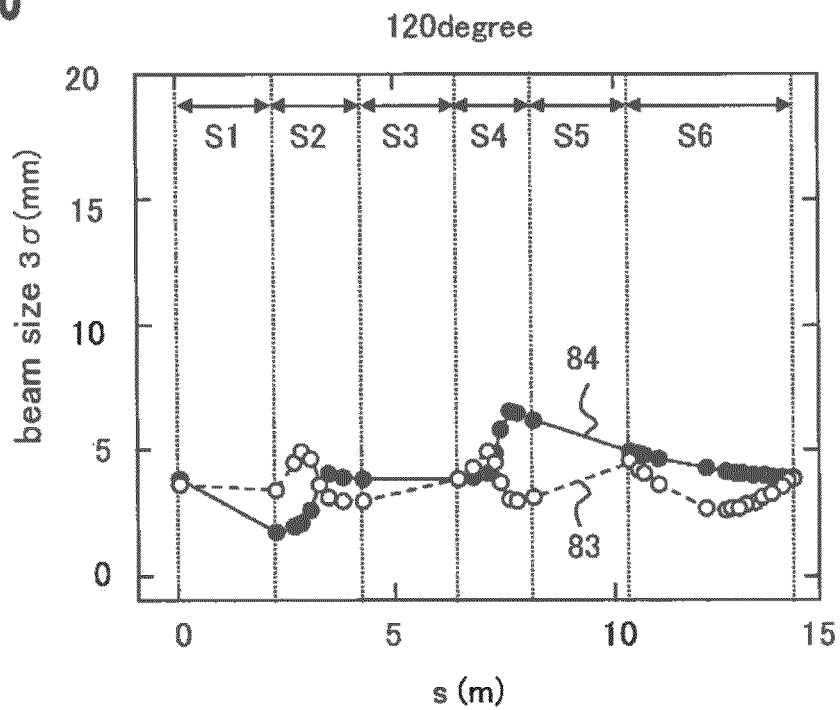
FIG. 36 is a graph representing the beam size when the angle of the rotating deflection unit according to Embodiment 2 of the present invention is 120°.
Figure 37:
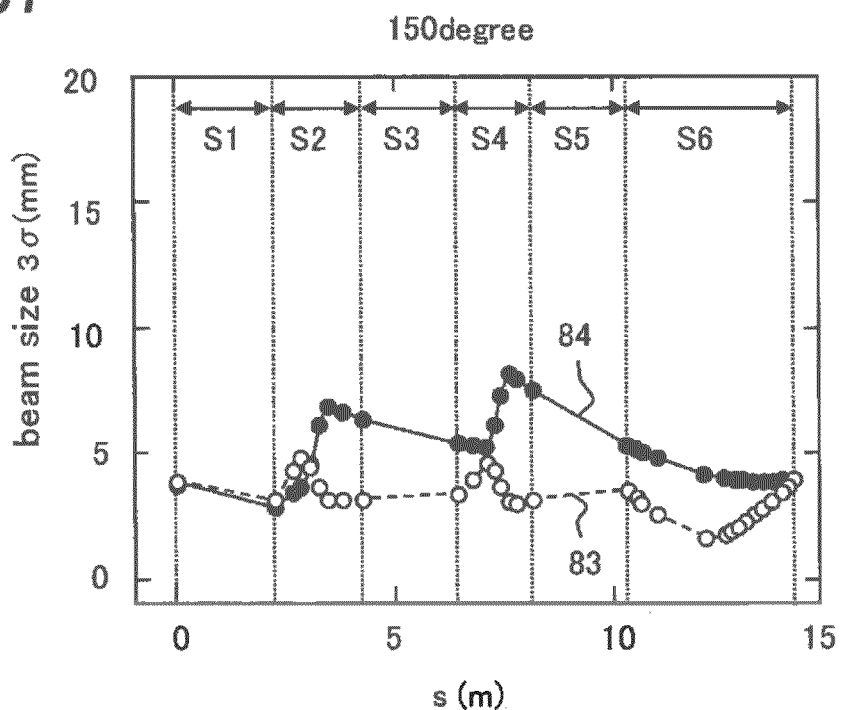
FIG. 37 is a graph representing the beam size when the angle of the rotating deflection unit according to Embodiment 2 of the present invention is 150°.

FIG. 31 is a graph representing the x-direction beam size when the angle of the rotating deflection unit according to Embodiment 2 of the present invention is 0°; FIG. 32 is a graph representing the y-direction beam size when the angle of the rotating deflection unit according to Embodiment 2 of the present invention is 0°. The x-direction characteristic 83 is the result obtained by simulating the x-direction phase space distribution as the linear distribution represented in FIG. 20A. The y-direction characteristic 84 is the result obtained by simulating the y-direction phase space distribution as an ellipsoidal distribution represented in FIG. 20B. The x-direction characteristic 85 is the result obtained by implementing simulation by use of x-direction Twiss parameters. The y-direction characteristic 86 is the result obtained by implementing simulation by use of y-direction Twiss parameters. In FIG. 31, the x-direction characteristic 83 and the x-direction characteristic 85 hardly coincide with each other. This suggests that when the x-direction phase space distribution is approximated with an ellipsoidal distribution, no accurate beam size is obtained. In FIG. 32, the y-direction characteristic 84 and the y-direction characteristic 86 coincide well with each other. In the section S1, the y-direction characteristic 84 and the y-direction characteristic 86 are deviated from each other; however, the deviation is neglectable.

In the rotating deflection unit 60 of the charged particle beam transport system 59 according to Embodiment 2, the limiting conditions "$\beta_x=\beta_y$ and $\alpha_x=\alpha_y$," are removed from the conditions at the inlet in the conventional designing and a predetermined x-direction phase space distribution is added thereto, without changing the strengths of the three deflection electromagnets 10a, 10b, and 10c and the four quadrupole electromagnets 11a, 11b, 11c, and 11d; thus, the rotation dependency of a beam size is cancelled at the isocenter IC. The predetermined x-direction phase space distribution is a linear phase space distribution, one end of which is the end-point coordinates (x, x') obtained by solving the equation (8) and the other end of which is the coordinates that is point-symmetry with the end-point coordinates (x, x') with respect to the origin, i.e., the coordinates (−x, −x'). As far as the predetermined x-direction phase space distribution is concerned, a quadrupole electromagnet is added to the fixed transport unit 61 of the charged particle beam transport system 59, or the positions of the quadrupole electromagnets are shifted and the excitation amounts are optimized again, so that a necessary particle distribution is realized at the inlet of the rotating deflection unit 60. In comparison with Embodiment 1, the charged particle beam transport system 59 according to Embodiment 2 can achieve the issue, with a few number of constraint conditions; thus, adjustment elements are decreased and hence the charged particle beam transport system 59 can further be downsized.

In the charged particle beam transport system 59 according to Embodiment 2, the foregoing predetermined x-direction phase space distribution is utilized as the x-direction phase space distribution at the inlet of the rotating deflection unit 60; therefore, even though asymmetry in the emittances exists at the inlet of the rotating deflection unit 60 of the charged particle beam transport system 59, a beam size having a small rotation dependency can be realized at the isocenter IC.

DESCRIPTION OF REFERENCE NUMERALS 10, 10a, 10b, 10c: deflection electromagnet
14: beam center line
15: gantry rotation axle
31: charged particle beam
45: irradiation subject
51: particle beam therapy system
54: accelerator
58, 58a, 58b: particle beam irradiation apparatus
59: charged particle beam transport system
60: rotating deflection unit
61: fixed transport unit
$\beta_x$, $\beta_y$, $\alpha_x$, $\alpha_y$: Twiss parameter
IC: isocenter

The invention claimed is:
1. A charged particle beam transport system that transports a charged particle beam to a particle beam irradiation apparatus mounted in a rotating gantry capable of rotating around an isocenter, the charged particle beam transport system comprising:
a rotating deflection unit that is mounted in the rotating gantry and rotates around a gantry rotation axle of the rotating gantry; and
a fixed transport unit ranging from an accelerator to the rotating deflection unit,
wherein letting an x direction denote a direction on a circular orbit plane of the accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam launched from the accelerator is a charged particle beam whose x-direction and y-direction emittances are different from each other,
wherein the rotating deflection unit includes two or more deflection electromagnets, the fixed transport unit includes two or more quadrupole electromagnets,
wherein when viewed from the gantry rotation axle, a gantry angle is defined as an angle between a beam center line of the particle beam irradiation apparatus and y-direction axis of the charged particle beam at an inlet of the rotating deflection unit,
wherein a gantry reference angle is defined as an angle of the rotating gantry at which the charged particle beam is transported in such a way that x-direction and y-direction emittances at the launching position of the accelerator are separated and the respective emittances are maintained,
wherein a first phase advance is defined as a change in a phase, of a phase space distribution of the charged particle beam, that advances when the charged particle beam travels from the inlet of the rotating deflection unit to the isocenter in the case where the gantry angle is the gantry reference angle,
wherein a second phase advance is defined as a change in a phase, of the phase space distribution of the charged particle beam, that advances when the charged particle beam travels from the inlet of the rotating deflection unit to the isocenter in the case where the gantry angle is turned by 90° from the gantry reference angle, and
wherein the fixed transport unit controls excitation amounts of the quadrupole electromagnets in such a way that a phase of the phase space distribution of the charged particle beam at the inlet of the rotating deflection unit coincides with a phase determined by a calculation based on an average value of the first phase advance and the second phase advance.

2. The charged particle beam transport system according to claim 1, wherein in the fixed transport unit, a phase of the phase space distribution of the charged particle beam at the inlet of the rotating deflection unit coincides with a phase based on an average value of a phase advance obtained by normalizing the first phase advance with respect to the 180° phase advance and a phase advance obtained by normalizing the second phase advance with respect to the 180° phase advance.

3. The charged particle beam transport system according to claim 2, wherein in the rotating deflection unit, x-direction and y-direction Twiss parameters thereof coincide with each other at the inlet and an outlet thereof.

4. A particle beam therapy system comprising:
a beam generation apparatus that generates a charged particle beam and accelerates the charged particle beam by means of an accelerator;
a charged particle beam transport system that transports the charged particle beam;
a particle beam irradiation apparatus that irradiates the charged particle beam transported by the charged particle beam transport system onto an irradiation subject; and
a rotating gantry that is equipped with the particle beam irradiation apparatus and can rotate around an isocenter,
wherein letting an x direction denote a direction on a circular orbit plane of the accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam accelerated by the accelerator is a charged particle beam whose x-direction and y-direction emittances are different from each other, and
wherein the charged particle beam transport system is according to claim 2.

5. The charged particle beam transport system according to claim 1, wherein in the fixed transport unit, a phase of the phase space distribution of the charged particle beam at the inlet of the rotating deflection unit coincides with a phase obtained by adding a minus sign to an average value of a phase advance obtained by normalizing the first phase advance with respect to 180° phase advance and a phase advance obtained by normalizing the second phase advance with respect to 180° phase advance.

6. The charged particle beam transport system according to claim 5, wherein in the rotating deflection unit, x-direction and y-direction Twiss parameters thereof coincide with each other at the inlet and an outlet thereof.

7. A particle beam therapy system comprising:
a beam generation apparatus that generates a charged particle beam and accelerates the charged particle beam by means of an accelerator;
a charged particle beam transport system that transports the charged particle beam;
a particle beam irradiation apparatus that irradiates the charged particle beam transported by the charged particle beam transport system onto an irradiation subject; and
a rotating gantry that is equipped with the particle beam irradiation apparatus and can rotate around an isocenter,
wherein letting an x direction denote a direction on a circular orbit plane of the accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam accelerated by the accelerator is a charged particle beam whose x-direction and y-direction emittances are different from each other, and
wherein the charged particle beam transport system is according to claim 5.

8. The charged particle beam transport system according to claim 1, wherein in the rotating deflection unit, x-direction and y-direction Twiss parameters thereof coincide with each other at the inlet and an outlet thereof.

9. The charged particle beam transport system according to claim 8, wherein in the rotating deflection unit, x-direction Twiss parameter $\beta_x$ and y-direction Twiss parameter $\beta_y$ coincide with each other and x-direction Twiss parameter $\alpha_x$ and y-direction Twiss parameter $\alpha_y$ coincide with each other at the inlet and the outlet thereof.

10. A particle beam therapy system comprising:
a beam generation apparatus that generates a charged particle beam and accelerates the charged particle beam by means of an accelerator;
a charged particle beam transport system that transports the charged particle beam;
a particle beam irradiation apparatus that irradiates the charged particle beam transported by the charged particle beam transport system onto an irradiation subject; and
a rotating gantry that is equipped with the particle beam irradiation apparatus and can rotate around an isocenter,
wherein letting an x direction denote a direction on a circular orbit plane of the accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam accelerated by the accelerator is a charged particle beam whose x-direction and y-direction emittances are different from each other, and
wherein the charged particle beam transport system is according to claim 9.

11. A particle beam therapy system comprising:
a beam generation apparatus that generates a charged particle beam and accelerates the charged particle beam by means of an accelerator;
a charged particle beam transport system that transports the charged particle beam;
a particle beam irradiation apparatus that irradiates the charged particle beam transported by the charged particle beam transport system onto an irradiation subject; and
a rotating gantry that is equipped with the particle beam irradiation apparatus and can rotate around an isocenter,
wherein letting an x direction denote a direction on a circular orbit plane of the accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam accelerated by the accelerator is a charged particle beam whose x-direction and y-direction emittances are different from each other, and
wherein the charged particle beam transport system is according to claim 8.

12. A particle beam therapy system comprising:
a beam generation apparatus that generates a charged particle beam and accelerates the charged particle beam by means of an accelerator;
a charged particle beam transport system that transports the charged particle beam;
a particle beam irradiation apparatus that irradiates the charged particle beam transported by the charged particle beam transport system onto an irradiation subject; and
a rotating gantry that is equipped with the particle beam irradiation apparatus and can rotate around an isocenter,
wherein letting an x direction denote a direction on a circular orbit plane of the accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam accelerated by the accelerator is a charged particle beam whose x-direction and y-direction emittances are different from each other, and wherein the charged particle beam transport system is according to claim 1.

13. A charged particle beam transport system that transports a charged particle beam to a particle beam irradiation apparatus mounted in a rotating gantry capable of rotating around an isocenter, the charged particle beam transport system comprising:

a rotating deflection unit that is mounted in the rotating gantry and rotates around a gantry rotation axle of the rotating gantry; and a fixed transport unit ranging from an accelerator to the rotating deflection unit, wherein letting an x direction denote a direction on a circular orbit plane of the accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam launched from the accelerator is a charged particle beam whose x-direction and y-direction emittances are different from each other, wherein the rotating deflection unit includes two or more deflection electromagnets, the fixed transport unit includes two or more quadrupole electromagnets, wherein the fixed transport unit decides x-direction phase space distribution of the charged particle beam at an inlet of the rotating deflection unit by controlling excitation amounts of the quadrupole electromagnets, wherein the x-direction phase space distribution is a distribution that can be approximated with a linear distribution calculated by use of a predetermined selection matrix, wherein the selection matrix is part of a transport matrix over a section from the inlet of the rotating deflection unit to the isocenter in the case where at the inlet and an outlet of the rotating deflection unit, x-direction and y-direction momentum dispersion functions are 0 and a gradient of the traveling direction, of the charged particle beam, that is perpendicular to the x direction and the y direction in the momentum dispersion function is 0; and the selection matrix has transport matrix elements $m_{11}$, $m_{12}$, $m_{33}$, and $m_{34}$ that link a position $(x_1, y_1)$ of a charged particle included in the charged particle beam at the inlet of the rotating deflection unit and a gradient $(x'_1, y'_1)$ of the traveling direction of the charged particle beam at the inlet of the rotating deflection unit with a position $(x_2, y_2)$ of the charged particle at the isocenter and a gradient $(x'_2, y'_2)$ of the traveling direction of the charged particle beam at the isocenter, and wherein letting $\sigma_y$ denote y-direction beam size at the isocenter, letting a first equation denote "$m_{11}x_0 + m_{12}x'_0 = \sigma_y$", and letting a second equation denote "$m_{33}x_0 + m_{34}x'_0 = \sigma_y$", one end point $(x_0, x'_0)$ and the other end point $(-x_0, -x'_0)$ of the linear distribution are calculated from the first and second equations.

14. The charged particle beam transport system according to claim 13, wherein in the rotating deflection unit, x-direction and y-direction Twiss parameters thereof coincide with each other at the inlet and the outlet thereof.

15. The charged particle beam transport system according to claim 14, wherein in the rotating deflection unit, x-direction Twiss parameter $\beta_x$ and y-direction Twiss parameter $\beta_y$ coincide with each other at the inlet and the outlet thereof.

16. A particle beam therapy system comprising:

a beam generation apparatus that generates a charged particle beam and accelerates the charged particle beam by means of an accelerator;

a charged particle beam transport system that transports the charged particle beam;

a particle beam irradiation apparatus that irradiates the charged particle beam transported by the charged particle beam transport system onto an irradiation subject; and a rotating gantry that is equipped with the particle beam irradiation apparatus and can rotate around an isocenter, wherein letting an x direction denote a direction on a circular orbit plane of the accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam accelerated by the accelerator is a charged particle beam whose x-direction and y-direction emittances are different from each other, and wherein the charged particle beam transport system is according to claim 15.

17. A particle beam therapy system comprising:

a beam generation apparatus that generates a charged particle beam and accelerates the charged particle beam by means of an accelerator;

a charged particle beam transport system that transports the charged particle beam;

a particle beam irradiation apparatus that irradiates the charged particle beam transported by the charged particle beam transport system onto an irradiation subject; and a rotating gantry that is equipped with the particle beam irradiation apparatus and can rotate around an isocenter, wherein letting an x direction denote a direction on a circular orbit plane of the accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam accelerated by the accelerator is a charged particle beam whose x-direction and y-direction emittances are different from each other, and wherein the charged particle beam transport system is according to claim 14.

18. A particle beam therapy system comprising:

a beam generation apparatus that generates a charged particle beam and accelerates the charged particle beam by means of an accelerator;

a charged particle beam transport system that transports the charged particle beam;

a particle beam irradiation apparatus that irradiates the charged particle beam transported by the charged particle beam transport system onto an irradiation subject; and a rotating gantry that is equipped with the particle beam irradiation apparatus and can rotate around an isocenter, wherein letting an x direction denote a direction on a circular orbit plane of the accelerator in a plane perpendicular to a traveling direction of the charged particle beam at a launching position of the accelerator and letting a y direction denote a direction perpendicular to the x direction in a plane perpendicular to the traveling direction of the charged particle beam, the charged particle beam accelerated by the accelerator is a charged particle beam whose x-direction and y-direction emittances are different from each other, and wherein the charged particle beam transport system is according to claim 13.

* * * * *